(12) United States Patent
Mascarenhas

(10) Patent No.: US 12,410,220 B2
(45) Date of Patent: Sep. 9, 2025

(54) MODULATION OF MAMMALIAN CELL LINEAGE BY SYNTHETIC IMMODULINS

(71) Applicant: Desmond Mascarenhas, Auburn, CA (US)

(72) Inventor: Desmond Mascarenhas, Auburn, CA (US)

( * ) Notice: Subject to any disclaimer, the term of this patent is extended or adjusted under 35 U.S.C. 154(b) by 0 days.

(21) Appl. No.: 18/264,181

(22) PCT Filed: Aug. 20, 2021

(86) PCT No.: PCT/US2021/046814
§ 371 (c)(1),
(2) Date: Aug. 3, 2023

(87) PCT Pub. No.: WO2022/191868
PCT Pub. Date: Sep. 15, 2022

(65) Prior Publication Data
US 2024/0327480 A1 Oct. 3, 2024

(51) Int. Cl.
| | |
|---|---|
| C07K 14/47 | (2006.01) |
| A61K 9/10 | (2006.01) |
| A61K 9/50 | (2006.01) |
| A61K 31/728 | (2006.01) |
| A61K 38/00 | (2006.01) |
| A61K 38/17 | (2006.01) |
| A61K 38/40 | (2006.01) |
| A61K 45/06 | (2006.01) |
| A61K 47/36 | (2006.01) |
| A61K 47/54 | (2017.01) |
| A61P 35/00 | (2006.01) |
| C07K 14/00 | (2006.01) |
| C07K 14/79 | (2006.01) |
| G01N 33/50 | (2006.01) |

(52) U.S. Cl.
CPC ............ *C07K 14/4743* (2013.01); *A61K 9/10* (2013.01); *A61K 9/5031* (2013.01); *A61K 31/728* (2013.01); *A61K 38/1754* (2013.01); *A61K 38/40* (2013.01); *A61K 45/06* (2013.01); *A61K 47/36* (2013.01); *A61K 47/542* (2017.08); *A61P 35/00* (2018.01); *C07K 14/001* (2013.01); *C07K 14/79* (2013.01); *G01N 33/5023* (2013.01); *G01N 33/5041* (2013.01); *A61K 38/00* (2013.01); *G01N 2333/4745* (2013.01)

(58) Field of Classification Search
None
See application file for complete search history.

*Primary Examiner* — Daniel C Gamett

(57) ABSTRACT

This invention provides synthetic immodulin peptides and related compositions and methods. The peptides of this invention exhibit new and surprising biological activities, such as the expansion of specified differentiated mammalian lineages from precursor cell populations which play important roles in post-apoptotic clearance, autoimmunity, targeted vaccination, cancer and trauma, by contacting mammalian cells with the synthetic peptides. Furthermore, the peptides of the invention can be made significantly more potent by each of a series of modifications described in the invention, including a carboxyterminal tripeptide extension to the canonical immodulin core sequence, other peptide extensions with kinase-inhibiting and other domains, substitution with modified amino acids, conjugation to certain bioactive small molecules, complexation to metals or glycosaminoglycans, and co-administration with helper molecules. The invention also teaches compositions and methods for enhancing previously disclosed uses of immodulin peptides to boost the efficacy of immodulin peptides in trauma, immune imbalance, cancer and other medically relevant conditions.

7 Claims, No Drawings
Specification includes a Sequence Listing.

MODULATION OF MAMMALIAN CELL LINEAGE BY SYNTHETIC IMMODULINS

This application claims benefit of international application number PCT/US2021/21433 with international filing date of 9 Mar. 2021. PCT/US2021/21433 claims priority to international application No. PCT/US2020/024828 with an international filing date of 26 Mar. 2020.

TECHNICAL FIELD

This invention relates to the field of peptide diagnostics and therapeutics, and more particularly to the use of insulin-like-growth-factor-binding-protein-sequence-derived synthetic "immodulin" peptides (also optionally referred to as "immodulator peptides") to increase the abundance of important mammalian cell lineages in vivo or ex vivo. The compositions and methods provided herein demonstrate new and surprising uses of improved extended immodulin peptides for treating mammals.

SUMMARY OF THE INVENTION

This invention provides synthetic immodulin peptides, originally derived from the sequences of classical insulin growth factor binding proteins (IGFBPs 1 through 6), and related compositions and methods. Insulin-like growth factors (IGFs) influence the growth and differentiation of mammalian cells. Unlike the full-length classical IGFBPs, whose primary function is to carry and deliver IGFs, the peptides of this invention are derived from less than 10% of the IGFBP amino acid sequence(s) and do not themselves bind IGFs. Thus, the effects of the synthetic immodulin peptides of this invention are unrelated to the effects of IGFs themselves. IGF-independent effects of classical IGFBPs have been known for decades, but there is no report of (IGF-independent) effects of IGFBP-derived peptides on monocyte differentiation, for example. The synthetic immodulin peptides disclosed herein exhibit new and surprising biological effects on cellular differentiation, such as the promotion of differentiated mammalian lineages from precursor cell populations. For example, compositions and methods are disclosed herein for increasing the abundance of CD169+, CCL22+, MHCII+, and certain C-lectin+ monocyte lineages by contacting precursor cells in vivo or ex vivo with synthetic immodulin peptides. Such monocyte differentiation activities have never been disclosed for IGFBP-derived synthetic peptides. For example, of the over 7000 scientific papers published on IGFBP-3 and IGFBP-3-derived peptides in the past forty years, none has demonstrated stimulation of differentiation of a specific monocyte lineage using synthetic peptides derived from IGFBP-3 (or any other classical IGFBP) sequence.

The invention describes the use of synthetic immodulin peptides to increase the abundance of mammalian cell lineages within a living animal or in a population of mammalian cells derived from an animal (i.e. in vivo or ex vivo). Importantly, the action of these peptides is IGF-independent, as the peptides do not bind IGFs. Cells treated with synthetic immodulin peptides ex vivo may subsequently be re-introduced into a living mammal. For example, hematopoietic or other mesenchymal cell lineages can be expanded so as to improve outcomes in cancer therapy, targeted vaccination, management of traumatic insults, anemia, neurodegeneration, regeneration of tissues, and prevention of medical complications from diseases such as obesity, diabetes, and diseases of aging.

Synthetic immodulin peptides are believed to rapidly target and enter cells, move to specific cellular compartments (e.g. the nucleus, ER, mitochondria), and interact with cellular machinery in different ways. For example, they may bind transcriptional factors and alter large transcriptional sets.

The use of short classical IGFBP-derived synthetic sequences to increase the abundance of hematopoietic cell lineages (such as CD169+, CCL22+, MHCII+ or specified C-lectin+ monocytes, dendritic cells and macrophages) has never been disclosed. As tools for accomplishing such targeted differentiation of mammalian cell precursors in vivo or ex vivo, the peptides of this invention are uniquely useful, for example, as adjuvants in cancer therapy, stimulating the body's response to vaccines and infectious agents, stimulation of erythropoiesis in anemia, modulation of osteoblast differentiation, or for stimulating the formation of neuroprotective cell types in the central and peripheral nervous systems. They may also be useful for the maintenance and repair of mammalian tissues such as islets of Langerhans, organs including thyroid, adrenal, thymus, lymph nodes, lung, heart, kidney, liver, spleen, ovaries, testis, intestine and brain, or for triggering appropriate differentiation of stem cells. Numerous other possible applications will be readily apparent to practitioners in the field.

As a biomarker of sepsis-related immunosuppression, decreased expression of monocyte HLA-DR (MHCII+) is considered a gold standard. Reduced numbers of HLA-DR+ monocytes have also been cited as markers of a major comorbidity of sepsis, compromised lung function. Lymph node (LN) subcapsular sinus (SCS) CD169+ macrophages, a newly recognized class of immunoregulatory macrophage, are at the frontline of immune defenses exposed to lymph-borne antigens, produce CCL22, and cross-prime effectors in both innate (dentritic) and adaptive (T-cells, B-cells) compartments via presentation of viral, microbial and cancer antigens captured from draining LNs and the marginal zone of the spleen. In lung, CCL22-producing CD169+ macrophages play a major homeostatic role in inflammatory events. Recent studies have shown that the LNs' SCS macrophage layer is interrupted in disease such as ARDS, cancer and kidney injury, frequently observed co-morbidities in post-traumatic immuno-dysfunctional states. Moreover, dendritic cell subpopulations defined by surface markers such as Clec9a, Clec10a, Clec12a, CD205, CD207 or CD 209 have recently been identified as useful in modulating targeted responses to vaccines.

Retinoid X receptors (RXRs) are promiscuous partners of heterodimeric associations with other members of the Nuclear Receptor (NR) superfamily. RXR ligands ("rexinoids") transcriptionally activate RXR homodimers or heterodimers such as RXRgamma/NR4A1. RXRs are obligatory partners for a number of other NRs, placing RXRs in a coordinating role at the crossroads of multiple signaling pathways. RXRs represent important targets for pharmacologic interventions and therapeutic applications. Receptor knockout studies demonstrate the important role for these receptors both during development and in adult differentiated tissues (cell proliferation, cell differentiation, cell death). These receptors also play an important regulatory role in metabolic signaling pathways (glucose, fatty acid and cholesterol metabolism), including metabolic disorders such as type 2 diabetes, hyperlipidemia and atherosclerosis. RXRs function as master regulators producing diverse physiological effects through the activation of multiple nuclear receptor complexes. Two important issues to consider in creating novel rexinoids to explore as clinical therapeutics include RXR-heterodimer selectivity and potency. The retinoid X receptor (RXR) subgroup (NR2B) of NRs is composed of 3 members: RXRα (NR2B1), RXRβ (NR2B2), and RXRγ (NR2B3). RXRα is detected in multiple tissues including muscle, liver, lung, in skin, intestine, epidermis and kidney, whereas RXRβ (NR2B2) is ubiquitously expressed. Unlike RXRα and β, RXRγ expression pattern is less widely spread. The transcriptional activity of RXR mainly results from its capacity to act as a cognate partner for other NRs. RXR can be generally engaged in 3 types of partnerships, permissive, conditional and non-permissive heterodimers. Non-permissive heterodimers, such as RXR/VDR (vitamin D receptor) and RXR/TR (thyroid hormone receptor), are activated only by agonists of the partner. Conditional heterodimers, such as RXR/RAR (retinoic acid receptor), are not activated by RXR agonists, but the activity of agonists of the RXR partner receptor is enhanced by RXR agonists (synergistic effect). RXR agonists alone, partner receptor agonists alone or a combination of both can activate permissive heterodimers. Such complexes include heterodimers formed with PPAR (peroxisome proliferator-activated receptor), FXR (farnesoid X receptor), LXR (liver X receptor), and the orphan NR4A group NRs Nur77 and Nurr1. The NR4A subgroup of nuclear receptors includes Nur77 (NR4A1, also known as NGFI-B or TR3), Nurr1 (NR4A2) and Nor-1 (NR4A3). Nur77 and Nurr1 transcriptional activities can be indirectly manipulated through modulation of their heterodimeric partner RXR, using rexinoids such a SR11237, BRF110, HX531 or HX600, or other RXR/NR4A ligands and modulators such as spironolactone, haloperidol, cytosporone B, C-DIM12, C-DIM8 and cilostazol.

Classical IGFBPs, from which the core sequences of the immodulin peptides of this invention are derived, are a highly conserved family of proteins, both structurally and functionally. The classical IGFBP gene repertoire has been identified in most vertebrate classes, including early-diverging protochordate lineages such as urochordates and cephalochordates. The sequence of IGFBPs 3, 5 and 6 from which the peptides of this invention are derived are particularly closely conserved. These three IGFBPs form a major evolutionary clade that diverged from IGFBPs 1, 2 and 4 before the R1 genome duplication event, approximately 700 million years ago, and before the development of the adaptive arm of the immune system. Functional features present in the 3/5/6 clade and not in the 1/2/4 clade include metal binding and nuclear transport. Amino acid sequence identity in the C-terminal thyroglobulin type-1 domain from which the sequences of the immodulin peptides of this invention are derived, which is present in all classical IGFBPs, is higher within the 3/5/6 IGFBP clade (for example, 59% between IGFBP-3 and -5, but only 31% between IGFBP-1 and -5). The inventor is not aware of any prior disclosure wherein any of the six canonical IGFBP proteins alone (without bound IGFs) were successfully used to drive the differentiation of specific monocyte lineages in mammalian cells. Regardless, this is the first demonstration that short synthetic peptides containing less than 10% of an IGFBP sequence can trigger mammalian cell differentiation, notably in cell types believed to be of critical importance to the functioning of the adaptive immune system. As disclosed herein for the first time, this medically and cosmetically useful feature is found in the sequences derived from IGFBPs 3, 5 and 6 (but not the IGFBPs 1, 2 or 4). This fact is consistent with the chronology of evolutionary divergence between the two major IGFBP clades i.e. prior to the development of the adaptive immune system. The immodulin peptide-3, -5, and -6 core sequences of this invention comprise, respectively:

```
                                            SEQ ID NO: 39
            GFYKKKQCRPSKGRKRGFCW

SEQ ID NO: 40
            GFYKRKQCKPSRGRKRGICW

SEQ ID NO: 41
            GFYRKRQCRSSQGQRRGPCW
```

This invention further provides improved C-terminally extended immodulin core sequences (extended by three residues at the carboxy terminus). Improved peptides containing such extended immodulin core sequences are sometimes termed extended immodulin peptides. The amino acid sequence of the extension is similar to the Cys-Val-Asp tripeptide, which is conserved at the corresponding position in the natural IGFBP-3/5/6 family. However, in the immX peptides of this invention, comprising SEQ ID Nos 5-7, core sequences are provided that differ from the natural sequences of known IGFBPs by the substitution of the cysteine residue in the ancient, evolutionarily conserved Cys-Val-Asp tripeptide of the natural sequences. Thus some peptides provided by this invention contain the extension XVD instead, where X is any amino acid other than cysteine. Furthermore, in some embodiments, the XVD tripeptide is located at the carboxy terminus of the synthetic peptide. Notably, in some of these embodiments, the XVD tripeptide consists of D-amino acids. The substitution of cysteine in the XVD tripeptide is a key alteration, from an industrial standpoint, as it removes the practical complication of having a third, unpaired cysteine in the synthetic peptide, which would be highly problematic for manufacturing. As shown in the Examples, the use of D-amino acids in the tripeptide of some embodiments is also a key improvement, providing higher stability in biological fluids and, apparently, better binding of glycosaminoglycans. The improved efficacy of immX peptides is clearly demonstrated in various in vivo and vitro experiments, as described in the Examples.

A BLASTp search of the human sequence database revealed no perfect matches for the immodulin core sequences containing the XVD tripeptide, where X is any amino acid other than cysteine. The immX-3, -5, and -6 core sequences (containing the XVD tripeptide) comprise:

```
                                            SEQ ID NO: 60
    GFYKKKQCRPSKGRKRGFCWXVD

SEQ ID NO:61
    GFYKRKQCKPSRGRKRGICWXVD

SEQ ID NO: 62
    GFYRKRQCRSSQGQRRGPCWXVD
    (where "X" is any amino acid except cysteine)
```

C-terminal regions of IGFBPs (but not the immX sequences themselves) have previously been implicated by mutational analysis in glycosaminoglycan-binding, caveolin-binding, transferrin-binding, collagen-binding, and retinoid X receptor-binding of the parent molecules. But it is important to note that the immX sequences disclosed here have never before been shown to be sufficient for those activities. Moreover, the immX sequences do not bind IGFs, so their effects on cellular differentiation are IGF-independent. This invention discloses, for the first time, among other facts: (a) the novel observation that immodulin peptides derived from IGFBPs 3, 5 and 6 can trigger IGF-independent differentiation of hematopoietic, neural and other mammalian cell lineages, in vivo or ex vivo; (b) the novel observation that the tripeptide XVD extension provides an unexpected and significant increase in potency to these peptides with regard to triggering mammalian cell differentiation, combating the immunological dysfunctions of severe trauma, as well as binding metals, glycosaminoglycans and other biologically relevant binding partners; (c) the novel observation suggesting that RXR/NR4A heterodimers are preferentially stimulated by the synthetic immX peptides of this invention, especially in the presence of certain helper molecules, notably some NR ligands; and (d) the novel observation that some immX peptides further extended by a kinase-inhibiting domain can show unexpected activities such as causing cell death in de-differentiated cancer cells, such as melanoma cells, and stimulating collagen synthesis in dermal fibroblasts.

Furthermore, synthetic immX peptides of this invention are made additionally potent by covalent attachment to small molecules. Of the dozens of small molecules tested for this purpose, only a few gave industrially useful yields under the harsh conditions of conventional peptide synthesis. This is a surprising and unforeseen result. Moreover, the small molecules successfully used in the couplings disclosed herein had not, in most cases, been previously reported as adducts of other peptides. Thus, success in the creation of this new class of chemically modified peptides under industrially useful manufacturing conditions is also trial-based, and clearly not obvious.

As disclosed in the present invention, new properties associated with improved metal binding to immX peptides are described. Unexpectedly, immX peptide-metal complexes show enhanced biological activities both in vitro and in vivo. This invention also discloses that metal-bound immX peptides (especially those additionally extended by a kinase-inhibitor domain) are substantially more potent in mammalian cell differentiation assays, and in triggering death of de-differentiated cell types such as some cancers e.g. melanoma. Substitution of D-amino acids in the immX extension tripeptide also increases peptide stability. The potent effects of combining better iron binding with enhanced stability using immX peptides in trauma models is disclosed here for the first time.

This invention discloses new compositions and new or improved utilities for the immodulin peptide class. Sequence extensions to immodulin core sequences disclosed in the invention confer new biological activities useful in treating human disease and in cosmetics (previously known utilities of immodulin peptides are described, for example, in PCT/US2020/024828, U.S. Pat. Nos. 5,519,003, 5,783,405, 6,165,977, 6,262,023, 6,342,368, 6,423,684, 6,855,693, 6,933,275, 7,393,835, 8,536,135, 10,369,1919; and references cited therein).

Methods disclosed in this invention include the administration of pharmaceutical compositions containing immodulin peptides to a mammal showing symptoms that may be linked to disease conditions, including but not limited to metabolic and cardiovascular diseases (especially those characterized by some underlying combination of insulin resistance, hyperglycemia, hypertension or hyperlipidemia); immune response to targeted vaccination, cancer progression and metastasis, pulmonary distress and acute kidney injury (AKI) in critical care settings, sepsis, anemia, systemic inflammatory conditions such as shock, post-operative oxidative stress such as after cardiopulmonary bypass or transplant, burns, blunt trauma, pancreatitis, rhabdomyolysis, xenobiotic stresses caused by cocaine, nicotine, alcohol, aminoglycoside antibiotics, cyclosporins, antiviral compounds or chemotherapeutic agents such as platinum compounds or doxorubicin; neuropathic pain and migraine; neurodegenerative diseases such as major depression, Parkinson's, Alzheimer's, Huntington's and ALS/Lou Gehrig's disease; immunosuppression phenomena; chronic obstructive pulmonary disease and other pulmonary diseases; pathological angiogenesis; impaired wound healing; ototoxicities; autoimmune conditions such as lupus erythematosus, arthritis, psoriasis, colitis, fibromyalgia, and multiple sclerosis; genetic diseases such as immune insufficiencies; cystinosis, Fanconi's and other conditions affecting mitochondrial respiration; other forms of mitochondrial dysfunction of bioenergetic failure; pulmonary diseases, especially chronic obstructive pulmonary disease, pulmonary arterial hypertension and asthma; ocular diseases such as cataracts and retinopathies, and conditions caused by infectious agents, including chronic viral infections such as hepatitis, influenza and coronavirus.

In one aspect, the invention provides a synthetic peptide, 20-60 amino acids in length, comprising: (i) a core immodulin sequence corresponding to one of SEQ ID NOs: 1-7; and, optionally, (ii) a small molecule of molecular mass less than one thousand daltons linked covalently to the amino terminus of the peptide.

In some embodiments the small molecule is selected from the group consisting of: oleic acid, eicosapentanoic acid, lauric acid, decanoic acid, lignoceric acid, docosahexanoic acid, 2-hydroxy-2-decenoic acid, phenolic acids, anthraquinones, pentacyclic triterpenoids, retinoic acids, adapalene, bexarotene and other rexinoids, rhein, proprionic acids, TLR4 inhibitors, keto acids, cinnamic acids, aromatic carboxylic acids, indoleacetic acids, xanthenes, xanthones, fenofibric acid, valproic acid, 2-hexyl-4-pentynoic acid, 2,7-dichlorodihydro-fluorescein diacetate, indolyl-carboxylic acids, ibuprofen, GIT-27, SR11237, MSA-2, SR-717, artemisinic acid and bromopyruvic acid.

In some embodiments a synthetic immodulin peptide is complexed or co-administered with a metal selected from the group consisting of: ferrous iron, ferric iron, zinc, copper, vanadium, ruthenium, cobalt, titanium, manganese and calcium, or chelates thereof.

In some embodiments a modified peptide described herein is complexed or co-administered with a glycosaminoglycan or other extracellular matrix component including a group consisting of: collagen, iron-binding proteins, gallocyanine, gallates, heparin, heparan sulfate, chondroitin sulfate, keratan sulfate, dermatan sulfate, and hyaluronate.

In a related aspect, the invention provides a pharmaceutical composition that includes any synthetic immodulin peptide or peptide complex described herein, and a pharmaceutically acceptable excipient.

In yet another related aspect the invention provides a method for treating a subject suffering from immunological, neurological, oncologic, skeletal, reproductive, metabolic or cosmetic dysfunction or imbalance, where the method includes administering to the subject (e.g., a human subject) a therapeutically effective dose of a synthetic immodulin peptide or immodulin peptide/helper molecule complex, or a pharmaceutical composition as described herein. In some embodiments the therapeutically effective dose of the synthetic immodulin peptide is from about 0.01 mg/kg/day to about 50 mg/kg/day.

In yet another related aspect, the invention provides an in vitro method for measuring the potency of any immodulin peptide described herein using cultured mammalian cells.

The compositions of the invention may be administered by means that include but are not limited to intravenous, oral, subcutaneous, intraarterial, intramuscular, intracardial, intraspinal, intrathoracic, intraperitoneal, intraventricular, sublingual, transdermal, and inhalation.

DETAILED DESCRIPTION

The terms "subject" and "individual", as used herein, refer to mammalian individuals, and more particularly to pet animals (e.g., dogs, cats), agricultural animals (e.g., cows, horses, sheep, and the like), and primates (e.g., humans).

The term "treatment" is used herein as equivalent to the term "alleviating", which, as used herein, refers to an improvement, lessening, stabilization, or diminution of a symptom of a disease or immune imbalance. "Alleviating" also includes slowing or halting progression of a symptom.

As used herein, "co-administration", "in conjunction with", "concurrent", or "concurrently", as used interchangeably herein, refers to administration of one treatment modality in addition to another treatment modality. As such, "in conjunction with" refers to administration of one treatment modality just before, during or soon after delivery of the other treatment modality to the subject.

The term "synthetic immodulin peptide" shall mean a peptide molecule 20-60 amino acids in length prepared by chemical synthesis and comprising any of SEQ ID NOs: 1-7.

The term "phytochemical" shall include D-heptomannulose, trehalose, naringin, resveratrol, polydatin, plumbagin, quercetin, curcumin, berberine, alpha-mangostin, wogonin, and ursolic acid.

The term "rexinoid" includes all ligands of RXRs, and conjugates thereof.

The term "bexarotene-class rexinoid" shall include bexarotene, LG100268, SR11237, HX600, HX531, BRF110 and conjugates thereof.

The term NSAID includes ibuprofen, sulindac (and its sulfide and sulfone derivatives), indomethacin, aspirin, naproxin, ketoprofen, ketorolac, diclofenac and etodolac, and conjugates thereof.

The term "RLR/STING/IFN-class agonist" shall include cyclic dinucleotides such as 2'3' cGAMP and cyclic di-GMP, nucleotides such poly-I:C and double-stranded ppp-RNA, and small molecule agonists such as G10, KIN1400, KIN1408, KIN 1148, RO8191, MSA-2, SR-717, alpha-mangostin, DMXAA and conjugates thereof.

The term "NR4A-class ligand" shall include spironolactone, haloperidol, cytosporone B, C-DIM5, C-DIM8, C-DIM12, cilostazol, PDNPA and conjugates thereof.

The term "immunomodulant-class molecule" shall include GIT-27, Schisandrin A, resiquimod (R-848), hydroxychloroquine, pidotimod, itraconazole, homoharringtonine, salidroside, celastrol, zymostenol, 7-dehydrocholesterol and conjugates thereof.

The term "Wnt-class molecule" shall include gallic acid, methyl gallate, gallocyanine, epigallocatechin gallate, XAV939, ethacrynic acid, leonurine and conjugates thereof.

The term "growth factor class molecule" shall include nerve growth factor (NGF), fibroblast growth factor (FGF), granulocyte-macrophage colony-stimulating factor (GM-CSF), and colony stimulating factor 1 (CSF1).

"Significantly increasing the abundance of a differentiated mammalian cell lineage" shall mean increasing the relative abundance of said differentiated cell lineage by at least fifteen percent over baseline via the methods of this invention as compared to an untreated population control such that the difference between the two populations is statistically significant, for example, with a calculated probability of $p<0.05$ using Student's T-test, or other comparable statistical test well known to those skilled in the art. "Differentiated mammalian cell lineage" means a reproducing mammalian cell population expressing markers characteristic of a differentiated cell type. "In vivo" treatment means treatment within a living animal. "Ex vivo" treatment means removal of a population of mammalian cells from an animal, treatment of said cells, and, optionally, re-introduction of said treated cells back into the animal. "Precursor cell", in the context of the invention, means a living mammalian cell capable of cellular growth or differentiation. "Circulatory cell lineage" includes cells of the blood and immune system, including hematopoietic, bone marrow and thymic cells. "Nervous cell lineage" includes cells of the central and peripheral nervous systems, eyes and ears. "Endocrine cell lineage" means cells of the hormone system, including pituitary, parathyroid, thyroid, adrenal and pancreas. "Integumentary cell lineage" means cells of the skin hair and subcutaneous tissue. "Musculoskeletal cell lineage" means cells of the bone, cartilage, ligaments, tendons and muscles. "Pulmonary cell lineage" means cells of the respiratory system, including lungs, trachea, larynx, nasal cavities and pharynx. "Cardiovascular cell lineage" means cells of the circulatory system, including the heart and blood vessels. "Gastrointestinal cell lineage" means cells of the digestive system, including stomach, intestinal tract, liver, pancreas, esophagus and salivary glands. "Lymphatic cell lineage" means cells of the lymphatic system, including spleen, lymph nodes, thymus and lymphatic vessels. "Reproductive cell lineage" means ovaries, uterus, mammary glands, testes, prostate and genitalia. "Urinary cell lineage" means cells of the kidneys, bladder and urethra.

"Significantly altering the relative abundance or bioactivity of a marker" means changing the abundance or biological activity of a protein, mRNA, carbohydrate, lipid, metabolite or other biological analyte whose changed abundance or bioactivity is measurable in a population of cells by practitioners skilled in the art using commercially available kits, wherein the change is shown to occur to a statistically significant degree compared to a control population of cells. The difference between the measured abundance or bioactivity of a marker is significantly different in a population of cells that received treatment via the methods of this invention as compared to an untreated population control if the difference between the two populations is statistically significant, for example, with a calculated probability of $p<0.05$ using Student's T-test, or other comparable statistical test well known in the art. The abundance or bioactivity of a marker, such as a protein or RNA known to be diagnostic for the differentiated cell population in question, can be readily measured using commercially available test kits, well-known and widely used in the field e.g. ELISA kits, qPCR kits, enzymatic activity kits, etc. Test kits can be purchased for cell surface markers such as CD169, Clec9a, Clec10a, Clec12a, CD205, CD207, CD209, CD209L and MHCII, secreted proteins such as IL-10, TGFbeta, TNFalpha, CCL22 and COL1A1 (collagen), and nuclear proteins such as FoxP3, Nur77/NR4A1, RXRs and their heterodimers with other nuclear receptors.

"RXR" means retinoid X receptor, and can refer to either the RXR gene or the protein it specifies. "Rexinoid" means a ligand of an RXR receptor. "RXRs" means any of the RXR isoforms, such as RXR-alpha, RXR-beta, RXR-gamma, and also covers heterodimers formed between them and other nuclear receptors such as NR4As. "NR4As" includes the orphan nuclear receptors NR4A1, NR4A2 and NR4A3, and can refer to either the NR4A gene or the protein it specifies. RXR receptors can and do form functional heterodimers with a variety of other nuclear receptors such as retinoic acid receptors (RARs), thyroid receptors (TRs), vitamin D receptor (VDR), liver X receptors (LXRs), peroxisome proliferator-activated receptors (PPARs), and the aforementioned NR4As.

"CD169" (also known as Siglec-1) means sialoadhesin, a cell adhesion molecule found on the surface of macrophages. Orthologs of this molecule in other mammalian species are included in this definition.

"C-lectins" means a C-type lectin such as Clec4a, Clec9a, Clec10a or Clec12a, and orthologs thereof.

"MHCII" means Class II major histocompatibility molecules such as HLA-DR and HLA-DQ and orthologs.

"CCL22" (also known as MDC) means C—C motif chemokine 22, and its orthologs.

"COL1A1" means alpha-1 Type I collagen.

"STING" means "stimulator of interferon genes. STING is also known as TMEM173.

"RLRs" means retinoic acid-inducible gene-I-like receptors.

"GSK3b" or "GSK3beta" refers to glycogen synthase kinase 3 beta. "GSK3a" or "GSK3alpha" refers to glycogen synthase kinase 3 alpha.

"Nur77" is the protein product of the NR4A1 gene. As an analyte, the two terms are here used interchangeably. Sometimes the gene product may be referred to as Nur77/NR4A1 or NR4A1/Nur77.

"TLR4 inhibitor" means an inhibitor of toll-like receptor 4 function.

The effects of synthetic immodulin peptides on mammalian cells are "IGF-independent" because, unlike the IGFBPs from which their core sequences are derived, the peptides of this invention do not bind IGFs.

This invention provides a method for significantly increasing the relative abundance of a differentiated mammalian cell lineage in vivo or ex vivo, comprising: (i) contacting one or more live mammalian cells in vivo or ex vivo with a synthetic immodulin peptide, 20-60 amino acids in length, comprising an amino acid sequence corresponding to any one of SEQ ID NOs: 1-4; and (ii) thereby significantly altering the relative abundance or bioactivity of a marker selected from the group consisting of GSK3beta, GSK3alpha, FoxP3, RNR4A1/Nur77, RXRs, RXR heterodimer, CD169, Clec9a, Clec10a, Clec12a, CD205, CD207, CD209, CD209L, MHCII, CCL22, IL-10, TNFalpha, TGF-beta and COL1A1 in said live mammalian cells, wherein said marker is distinctive for said differentiated mammalian cell lineage. More preferably, the mammalian cell lineage of the invention is a hematopoietic cell lineage. Even more preferably, the mammalian cell lineage of the invention is a monocytic cell lineage.

This invention also provides a peptide having an amino terminus formed by covalent linkage to a "small molecule" of molecular mass less than one thousand daltons, preferably less than five hundred daltons. Said "small molecule" is selected from the group consisting of oleic acid, eicosapentanoic acid, lauric acid, decanoic acid, lignoceric acid, docosahexanoic acid, 2-hydroxy-2-decenoic acid, phenolic acids, anthraquinones, pentacyclic triterpenoids, retinoic acids, adapalene, rexinoids (e.g. bexarotene, SR11237, BRF110, HX531, HX600, rhein, sulindac), proprionic acids, TLR4 inhibitors, keto acids, cinnamic acids, aromatic carboxylic acids, indoleacetic acids, xanthenes, xanthones, fenofibric acid, valproic acid, 2-hexyl-4-pentynoic acid, 2,7-dichlorodihydro-fluorescein diacetate, indolyl-carboxylic acids, ibuprofen, GIT-27, MSA-2, SR-717, artemisinic acid and bromopyruvic acid.

The invention also provides a synthetic immodulin peptide comprising a core sequence selected from the group consisting of any of SEQ ID NOs: 1-7. In some embodiments, said core sequence is aminoterminally extended by a sequence selected from the group consisting of sequence IDs 8-12.

In some embodiments the invention provides a synthetic immX peptide, 20-60 amino acids in length, comprising an amino acid sequence corresponding to any of SEQ ID NOs: 5-7, having Xaa-Val-Asp at the peptide carboxy terminus wherein Xaa is D-alanine, D-serine or glycine. In some embodiments the invention provides a synthetic immX peptide, 20-60 amino acids in length, comprising an amino acid sequence corresponding to any of SEQ ID NOs: 5-7, having Xaa-Val-Asp at the peptide carboxy terminus wherein Xaa is D-alanine or D-serine. These end-modifications are preferred embodiments of the invention.

In some embodiments the invention provides kinase inhibitor peptide sequences to be used in conjunction with the core immodulin sequences of this invention. Kinase inhibitor peptides have been widely used by practitioners in the field for several decades. For example, U.S. Pat. No. 5,783,405 lists dozens of peptide sequences and teaches their use as protein kinase C inhibitors. Among them are the sequences AFNSYELGS (SEQ ID NO: 9) and SLNPEWNET (SEQ ID NO: 8), claimed to inhibit PKC-delta and PKC-beta, respectively.

In some embodiments the invention provides a therapeutic immodulin peptide complexed with metal, wherein said metal is selected from the group consisting of ferrous iron, ferric iron, zinc, copper, vanadium, ruthenium, cobalt, titanium, manganese, and calcium, or metallocene compounds containing these metals. In other embodiments, the invention provides a therapeutic immodulin peptide complexed with a component of the extracellular matrix such as collagen, iron-binding proteins or a glycosaminoglycan such as heparin, heparan sulfate, chondroitin sulfate, keratan sulfate, dermatan sulfate, and hyaluronate.

In another aspect, the invention provides a method for treating a mammal showing symptoms of immune dysfunction or imbalance comprising administering to said mammal via intramuscular, subcutaneous, parenteral, transdermal, intranasal, intravenous or intrathecal route of administration a pharmaceutical formulation comprising a therapeutically effective dose of an immodulin peptide according to the invention, and a pharmaceutically acceptable excipient, thereby alleviating said symptoms of dysfunction. In some embodiments, the immodulin peptide is administered in a therapeutically effective dose of peptide between about 0.01 mg/kg/day to about 50 mg/kg/day.

In another aspect, the invention provides for co-administration of a helper molecule that modulates the activity of cellular antiviral defenses. Preferably, said helper molecule is a modulator of the activity of cellular antiviral defenses, said helper selected from the group consisting of modulators of RIG-I, MDA5, MAVS, STING, IRF3, STAT1, STAT3, TBK1, PACT, LGP2, NFkappaB, DNA methylases such as 5-azacytidine or SAHA and toll-like receptors. Demethylation of DNA can derepress endogenous retroviral sequences which then, in turn, trigger cellular antiviral defense mechanisms. Preferably, the helper molecule is an agonist of RIG-I or MDA5 such as poly(I:C). Many agonists and enhancers of helper molecules are well-known in the art such as KIN-1400, a synthetic RIG-I agonist commercially available from Cayman Chemical (Ann Arbor, MI).

This invention envisages an in vitro method for measuring cell differentiating potency of a synthetic immodulin peptide, the method comprising measurement of the abundance of a marker selected from the group consisting of RXRs, NR4As, CD169, C-lectins, MHCII, CCL22, COL1A1, STING, interferons, RLRs, Wnt, RANK or toll-like receptors in cultured mammalian cells that have been treated with the synthetic peptide. As will be understood by those of skill in the art, the mode of detection of a diagnostic signal will depend on the detection system utilized in the assay. For example, if a fluorescent detection reagent is utilized, the signal may be measured using a technology capable of quantitating the signal from the sample, such as by the use of a fluorometer. If a chemiluminescent detection system is used, then the signal will typically be detected using a luminometer. Methods for detecting signal from detection systems are well known in the art and need not be further described here.

Sequence "identity" and "homology", as referred to herein, can be determined using BLAST, particularly BLASTp as implemented by the National Center for Biotechnology Information (NCBI), using default parameters. It will be readily apparent to a practitioner skilled in the art that sequences claimed hereunder include all homologous and trivial variants of an immodulin peptide, such as by conservative substitution, extension and deletion in amino acid sequence. Trivial substitution variants include swapping of an amino acid with another belonging to the same class, without such substitution resulting in statistically and functionally significant change. "Classes" of amino acids include positively charged amino acids (arginine, lysine, histidine), negatively charged amino acids (aspartic acid, glutamic acid), aromatic amino acids (tyrosine, phenylalanine, tryptophan), branched chain amino acids (valine, leucine isoleucine) and other natural groupings such as (serine, threonine) and (asparagine, glutamine). For the purposes of this invention, such conservative substitutions to immodulin sequences, if they do not create a significant change in function, are considered equivalent to the original and are covered by the scope of this invention.

For testing efficacy of pharmaceutical composition containing an immodulin peptide, an effective amount of therapeutic agent is administered to a subject having a disease. In some embodiments, the agent is administered at about 0.001 to about 50 milligrams per kilogram total body weight per day (mg/kg/day). In some embodiments the agent is administered at about 0.001 to about 50 mg/kg/day, e.g., 0.01, 0.015, 0.02, 0.05, 0.1, 0.2, 0.5, 0.7, 1, 2, 4, 5, 7, 9, 10, 15, 20, 25, 30, 35 or another dose from about 0.001 mg/kg/day to about 50 mg/kg/day.

Therapeutic agents are preferably administered via oral or parenteral administration, including but not limited to intravenous (IV), intra-arterial (IA), intraperitoneal (IP), intramuscular (IM), intracardial, subcutaneous (SC), intrathoracic, intraspinal, intradermal (ID), transdermal, oral, sublingual, inhaled, and intranasal routes. IV, IP, IM, and ID administration may be by bolus or infusion administration. For SC administration, administration may be by bolus, infusion, or by implantable device, such as an implantable minipump (e.g., osmotic or mechanical minipump) or slow release implant. The agent may also be delivered in a slow release formulation adapted for IV, IP, IM, ID or SC administration. Inhaled agent is preferably delivered in discrete doses (e.g., via a metered dose inhaler adapted for protein delivery). Administration of a molecule comprising an agent via the transdermal route may be continuous or pulsatile. Administration of agents may also occur orally. For parenteral administration, compositions comprising a therapeutic agent may be in dry powder, semi-solid or liquid formulations. For parenteral administration by routes other than inhalation, the composition comprising an agent is preferably administered in a liquid formulation. Compositions comprising an agent formulation may contain additional components such as salts, buffers, bulking agents, osmolytes, antioxidants, detergents, surfactants, and other pharmaceutical excipients as are known in the art.

As will be understood by practitioners skilled in the art, the symptoms of disease alleviated by the instant methods, as well as the methods used to measure the symptom(s) will vary, depending on the particular disease and the individual patient.

EXAMPLES

Example 1. Enhanced Metal Binding by Immodulin Peptides with C-Terminal Tripeptide Extension N-terminally biotinylated versions of the peptides listed below were used in ferric iron-binding assays involving either an Alexa488-labeled streptavidin protocol (Binding Assay 1) or FITC-NTA assay (Binding Assay 2). Fluorescence was standardized to binding with immX3AVD control peptide (100) and the average of multiple experiments using both protocols is shown. P values are shown relative to the control immX3AVD peptide (**<0.05). D-amino acid residues are underlined in the sequences and the extension tripeptide of immX peptides is shown in bold font. Binding Assay 1 was done as follows: NTA coated 96-well plates (G-Biosciences, St. Louis, MO) were charged with ferric chloride and contacted with equimolar biotinylated peptide:streptavidin-A488 complex (400 ng peptide per well) for 60 min at room temperature, washed with phosphate-buffered saline (PBS) and read at 525 nM in a fluorescence counter. Binding Assay 2 was done as follows: Streptavidin coated 96-well plates (G-Biosciences, St. Louis, MO) were contacted with 400 ng peptide per well in PBS buffer for 60 minutes at room temperature, washed in PBS, then contacted with FITC-NTA (TRC, Toronto, Canada) complexed with equimolar ferric chloride (10× molar equivalent per well) for 60 min at room temperature, washed with PBS and read at 525 nM in a fluorescence counter. Results of ferric iron binding experiments using Assay 1 (n=number of experiments averaged) are shown in the table below:

| PEPTIDE | SEQUENCE | n | Avg ± SD | SEQ ID NO: |
|---|---|---|---|---|
| None (buffer) | | 1 | 3.2 ± 3.6** | |
| imm1 | KNGFYHSRQCETSMDGEAGLCW | 2 | 2.5 ± 1.6** | 42 |
| imm2 | KHGLYNLKQCKMSLNGQRGECW | 2 | 1.6 ± 0.8** | 43 |

-continued

| PEPTIDE | SEQUENCE | n | Avg ± SD | SEQ ID NO: |
|---|---|---|---|---|
| imm3 | KKGFYKKKQCRPSKGRKRGFCW | 5 | 66.7 ± 4.7** | 44 |
| imm4 | RNGNFHPKQCHPALDGQRGKCW | 5 | 3.3 ± 1.5** | 45 |
| imm5 | RKGFYKRKQCKPSRGRKRGICW | 5 | 71.6 ± 6.6** | 46 |
| imm6 | HRGFYRKRQCRSSQGQRRGPCW | 2 | 65.9 ± 4.9** | 47 |
| immX3AVD | KKGFYKKKQCRPSKGRKRGFCWAVD | 5 | 100.0 | 13 |
| immX4AVD | RNGNFHPKQCHPALDGQRGKCWAVD | 2 | 1.2 ± 1.3** | 48 |
| immX5AVD | RKGFYKRKQCKPSRGRKRGICWAVD | 2 | 88.1 ± 14.2 | 15 |
| immX3dAVD | KKGFYKKKQCRPSKGRKRGFCW(dA)VD | 1 | 108.1 ± 1.5 | |
| immX3dAdVdD | KKGFYKKKQCRPSKGRKRGFCW(dA)(dV)(dD) | 2 | 102.4 ± 9.1 | |
| immX3dSdVdD | KKGFYKKKQCRPSKGRKRGFCW(dS)(dV)(dD) | 2 | 133.6± | |
| immX3FVS | KKGFYKKKQCRPSKGRKRGFCWFVS | 2 | 78.3 ± 6.5** | 49 |
| immX3RVD | KKGFYKKKQCRPSKGRKRGFCWRVD | 4 | 97.5 ± 5.1 | 50 |
| immX3K1dAdVdD | SLNPEWNETKGFYKKKQCRPSKGRKRGFCW(dA)(dV)(dD) | 4 | 108.2 ± 6.6 | |

Example 2. Enhanced Mammalian Cell Differentiation by immX Peptides

Mammalian cell differentiation assays using THP1-Dual monocytes reporter cell line (Invivogen Inc, San Diego, CA) seeded at 2×10e5 cells per well in 96-well plates and cultured at 37 degrees C. in RPMI-1640 growth medium plus 10% fetal bovine serum and 1% penicillin/streptomycin, then treated for 24 hours with either 100 ng/ml Phorbol 12-myristate 13-acetate (PMA protocol; Cayman Chemical Company, Ann Arbor, MI) or a mixture of IL-4 (100 ng/ml), GM-CSF (100 ng/ml), TNF-alpha (20 ng/ml) and ionomycin (200 ng/ml) (Cytokine protocol; Peprotech, Rocky Hill, NJ). Peptide (330 nM) was then added, and incubation continued for an additional 24 hours. Culture supernatants were then assayed for CCL22. Plates with adherent cells were washed with PBS and assayed for immunoreactivity of surface markers such as CD169, Clec9a, Clec12a or MHCII using fuorescent tag- or biotin-labeled anti-human antibodies purchased from Miltenyi Biotec (Auburn, CA) and a relevant secondary detection reagent, or by fluorescent counts. Results were expressed as arbitrary units relative to the control immX3AVD peptide, and p values were also calculated and shown relative to the control immX3AVD peptide (values significantly above background are shown in bold font; **p<0.05 versus immX3AVD control; AU=arbitrary immunoreactivity units relative to control, avg±SD). These results show why synthetic immX peptides comprising an amino acid sequence corresponding to any of SEQ ID NOs: 5-7 and having Xaa-Val-Asp at the peptide carboxy terminus wherein Xaa is D-alanine or D-serine, are preferred embodiments of the invention.

| PEPTIDE | CD169+ (AU)# | CCL22 pg/ml # | Clec12A(AU)## |
|---|---|---|---|
| None (buffer) | 1.2 ± 1.1** | 17.1 ± 1.2** | 0.5 ± 3.2** |
| imm1 | 3.1 ± 2.2** | n.d. | n.d. |
| imm2 | 3.0 ± 0.5** | n.d. | n.d. |
| imm3 | 27.8 ± 3.0** | 55.3 ± 16.1** | n.d. |
| imm4 | 3.8 ± 1.1** | n.d. | n.d. |
| imm5 | 36.5 ± 3.0** | n.d. | n.d. |
| imm6 | 19.9 ± 2.3** | n.d. | n.d. |
| immX3AVD | 100 | 282.4 ± 18.4 | 100 |
| immX4AVD | 1.0 ± 0.3** | n.d. | n.d. |
| immX5AVD | 100.9 ± 3.5 | 228.6 ± 8.1 | n.d. |
| immX3dAVD | 104.3 ± 6.1 | 247.3 ± 16.1 | n.d. |
| immX3dAdVdD | 183.3 ± 6.4** | n.d. | 106.6 ± 5.2 |
| immX3dSdVdD | 145.7 ± 9.3** | n.d. | n.d. |
| immX3FVS | 109.4 ± 4.5 | 251.3 ± 5.8 | n.d. |
| immX3RVD | 88.1 ± 4.2 | 272.5 ± 35.7 | n.d. |
| immX3K1dAdVdD | 249.3 ± 13.9** | 135.8 ± 24.2** | 321.9 ± 25.6** |

AU: arbitrary units (immunoreactivity);
PMA protocol;
cytokine protocol;
n.d. = not determined

Example 3. Adjuvant Effect of Other Molecules on immX Peptide Potency in THP1-Dual Assay The THP1-Dual cell differentiation assay was carried out as described above in Example 2, using immX3 peptide (330 nM) in all samples plus the indicated helper or inhibitor molecule. AU=arbitrary ELISA units. **p<0.01.

| HELPER | CAS# | CLASS | [CONC] | CD169 (AU) |
|---|---|---|---|---|
| None (buffer) | | | | 100.0 ± 4.9 |
| Hyaluronic acid | | glycosaminoglycan | 0.6 ug/ml | 110.5 ± 10.2 |
| Heparin | | glycosaminoglycan | 1.0 ug/ml | 34.1 ± 2.9** |
| Transferrin | | Fe-binding protein | 0.8 ug/ml | 126.8 ± 9.3** |
| Toosendanin | 58812-37-6 | GSK3b agonist | 2 uM | 188.2 ± 16.3** |
| Supercinnamaldehyde | 70351-51-8 | C/EBPb inhibitor | 2 uM | 159.7 ± 16.6** |
| Bisindolylamide | 138489-18-6 | PKC inhibitor | 2 uM | 130.1 ± 8.4** |
| RIG-I agonist [a] | | RIG-I agonist | 1 ug/ml | 135.4 ± 9.1** |
| RIG-I agonist [b] | 446826-86-4 | RIG-I agonist | 2 uM | 131.6 ± 4.6** |
| G10 | 702662-50-8 | STING agonist | 2 uM | 143.4 ± 17.8** |
| 2'3'-cGAMP | | Cyclic dinucleotide | 15 uM | 168.5 ± 10.9** |
| Cyclic-di-GMP | | Cyclic dinucleotide | 15 uM | 142.9 ± 9.7** |
| D-mannoheptulose | | Phytochemical | 50 uM | 140.8 ± 12.4** |
| Calcitriol | 32222-06-3 | VDR agonist | 2 uM | 102.0 ± 11.3 |
| Spironolactone | 52-01-7 | RXR or NR4A ligand | 2 uM | 120.1 ± 10.5** |
| C-DIM12 | 178946-89-9 | RXR or NR4A ligand | 2 uM | 119.0 ± 3.7** |
| C-DIM8 | 151358-47-3 | RXR or NR4A ligand | 2 uM | 91.0 ± 24.8 |
| Clobetasol | 25122-46-7 | RXR or NR4A ligand | 2 uM | 98.5 ± 5.5 |
| Cilostazol | 73963-72-1 | RXR or NR4A ligand | 2 uM | 99.4 ± 27.7 |
| Cytosporone B | 321661-62-5 | RXR or NR4A ligand | 2 uM | 120.3 ± 6.4** |
| Dihydroergotamine | 6190-39-2 | RXR or NR4A ligand | 2 uM | 170.3 ± 20.7** |
| 6-mercaptopurine | 6112-76-1 | RXR or NR4A ligand | 2 uM | 104.9 ± 4.0 |
| Bexarotene | 153559-49-0 | RXR or NR4A ligand | 2 uM | 96.9 ± 6.8 |
| LG100268 | 153559-76-3 | RXR or NR4A ligand | 2 uM | 76.8 ± 11.9** |
| HX600 | 172705-89-4 | RXR or NR4A ligand | 2 uM | 110.5 ± 19.0 |
| HX531 | 188844-34-0 | RXR or NR4A ligand | 2 uM | 90.4 ± 6.2 |
| Cyclosporine A | | NFAT inhibitor | 2 uM | 128.9 ± 6.7** |
| GM-CSF | | Growth factor class | 0.1 ug/ml | 147.0 ± 15.3** |
| CSF1 | | Growth factor class | 0.1 ug/ml | 108.0 ± 32.3 |
| Leptin | | Growth factor class | 1.0 ug/ml | 103.3 ± 11.6 |
| GIT27 | 6501-72-0 | TLR4 inhibitor | 2 uM | 166.5 ± 34.1** |

[a] Invivogen Inc. (San Diego, CA) Cat. # tlrl-3pmnalv
[b] Cayman Chem. Co. (Ann Arbor, MI) Cat. # 22441

Example 4. Binding to RXRs and Nur77 (NR4A1)

Experiment 4A. Binding of immodulin peptides to AA111-228 DNA-binding domain of RXR-alpha (RXRa-DBD). 1 ug/well recombinant RXRa-DBD (Abcam, Cambridge, MA) was adsorbed to wells of a 96-well plate for 60 minutes at room temperature, then blocked with 200 uL 1% bovine serum albumin (BSA) in PBS buffer overnight. Plate was washed and 800 ng/well Streptavidin-Alexa 488 conjugate (SA488)-labelled immX peptide was added. The plate was incubated for 60 min at room temperature, washed and counted in a standard fluorometer (excitation/emission 485/525 nm). Background (buffer alone) was subtracted. The results show that imm3, imm5 and imm6 bind RXRa-DBD. *p<0.05, **p<0.01 vs no peptide; (Peptide/Fluorescence) imm1: 670±85*; imm2: 2±38; imm3: 6,572±129; imm4: 27±31; imm5: 6,802±336; imm6: 587±192*; No peptide: 8±232.

Experiment 4B. Binding of immodulin peptides to RXR isoforms and domains. 100 ng/well recombinant human RXRa-DBD or RXRa-LBD, or 400 ng/well full length RXR-alpha, RXR-beta, RXR-gamma or PPAR-gamma (Abcam, Cambridge, MA) was adsorbed to wells of a 96-well plate for 60 minutes at room temperature, then blocked with 200 uL 1% BSA in PBS buffer overnight. The plate was washed with PBS and 800 ng/well Streptavidin-Alexa 488 conjugate (SA488)-labelled peptide was added. The plate was incubated for 2 hours at room temperature, washed and counted in a fluorometer (excitation/emission 485/525 nm). The results are expressed relative to imm3 binding (=100) and are shown in the table below. Significant binding above background is also shown (**p<0.05). The results indicate that imm3, imm5 and imm6 bind RXR-alpha and -gamma (especially RXR-gamma). When tested against domains of RXR-alpha, these peptides bind the DNA-binding domain (DBD) better than the ligand-binding domain (LBD).

| RXR | No peptide | imm3 | imm4 | imm5 | imm6 |
|---|---|---|---|---|---|
| None | 0.8 ± 0.4 | 1.3 ± 1.2 | 1.3 ± 1.7 | 1.2 ± 2.8 | 0.6 ± 1.1 |
| RXR-alpha | 1.2 ± 0.3 | 11.2 ± 1.0** | 3.6 ± 1.3 | 17.2 ± 0.3** | 12.9 ± 0.5** |
| RXR-beta | 2.3 ± 0.7 | 2.9 ± 1.1 | 0.3 ± 1.2 | 4.0 ± 0.8 | 4.7 ± 0.4 |
| RXR-gamma | 2.6 ± 0.3 | 100.0 ± 16.5** | 3.6 ± 7.0 | 90.0 ± 19.6** | 42.0 ± 11.6** |
| PPAR-gamma | 0.9 ± 0.4 | 2.1 ± 1.4 | 0.1 ± 0.0 | 1.6 ± 0.4 | 6.8 ± 2.0 |
| RXR-alpha DBD | 2.2 ± 0.4 | 22.2 ± 2.4** | 3.2 ± 2.0 | 22.7 ± 3.1** | 22.9 ± 2.1** |
| RXR-alpha LBD | 1.8 ± 0.1 | 0.6 ± 1.5 | 3.0 ± 1.3 | 1.8 ± 1.9 | 1.6 ± 1.4 |

Experiment 4C. Binding of Immodulin Peptides to Full-Length Human Nur77 (NR4A1).

400 ng/well recombinant human Nur77 protein (NR4A1) purchased from Abcam Inc, Cambridge, MA, was adsorbed to wells of a 96-well plate for 90 minutes at room temperature, then blocked with 200 uL 1% BSA in PBS buffer overnight. The plate was washed with PBS and then 333 ng/well Streptavidin-Alexa 488 conjugate (SA488)-labelled imm3 or imm4 peptide was added. The plate was incubated for 60 min at room temperature, washed and counted in a standard fluorometer (excitation/emission 485/525 nm). Background (buffer alone) was subtracted. The results (normalized to imm3 binding=100) are shown in the table below. They show that imm3 but not imm4 binds Nur77. **$p<0.01$ vs no Nur77 control.

| Nur77 (NR4A1) | imm3 | imm4 |
|---|---|---|
| None | 1.7 ± 2.7 | 2.9 ± 3.3 |
| 400 ng | 100.0 ± 9.3** | 0.3 ± 8.9 |

Experiment 4D. Binding of Immodulin Peptides to Glycosaminoglycans.

Streptavidin-coated 96-well plates (G-Biosciences, St. Louis, MO) were pre-treated with biotinylated peptides [see Example 1 for key] at 1 ug/well, at room temperature for 60 minutes. The plate was washed with PBS buffer and then 1 ug FITC-labelled heparin or hyaluronic acid in 100 uL PBS buffer was added per well (all tests in quadruplicate). Incubation proceeded for 90 minutes at room temperature, followed by two PBS washes. The plate was read in a standard laboratory fluorometer (488/525 nm exitation/absorbance) and the counts normalized for immX3 peptide binding=100. Values statistically above background are shown in bold font. **$p<0.05$ versus immX3AVD.

| PEPTIDE | Heparin | Hyaluronate |
|---|---|---|
| imm2 | 27.4 ± 22.9 | 3.1 ± 9.8 |
| imm3 | 104.2 ± 22.0 | 57.2 ± 5.7** |
| imm4 | 6.8 ± 24.1 | 14.6 ± 22.6 |
| imm5 | 95.1 ± 25.7 | 60.0 ± 8.6** |
| imm6 | 97.2 ± 17.3 | 44.9 ± 14.1** |
| immX3AVD | 100.0 ± 4.7 | 100.0 ± 22.8 |
| immX4AVD | 7.3 ± 17.1 | 61.1 ± 34.1 |
| immX5AVD | 68.7 ± 26.2 | 113.9 ± 15.7 |
| immX3dAdVdD | 55.5 ± 5.7 | 104.2 ± 14.7** |
| immX3K1dAdVdD | 56.0 ± 7.3 | 101.9 ± 16.4** |

Example 5. Potentiating Effects of C-Terminal Tripeptide Extension on Peptide Stability and the Systemic Efficacy of sV-Nephrilin and Traumatin-3N1A immX Peptides in Burn Trauma Experiment 5A. V-nephrilin peptide (imm3N1V) is a designed inhibitor of Rictor complex, an evolutionarily conserved assembly believed to modulate responses to cellular stress. We previously demonstrated the ability of nephrilin peptide to suppress neuroinflammation, loss of body mass, glycemic control and kidney function in a rat scald model, as well as sepsis mortality in a mouse model. The tripeptide extension of V-nephrilin peptide is sV-nephrilin (tripeptide extension in sV-nephrilin is underlined):

```
imm3N1V (V-nephrilin):
                                        (SEQ ID NO: 51)
RGVTEDYLRLETLVQKVVSKGFYKKKQCRPSKGRKRGFCW immX3N1sV (sV-nephrilin):
                                        (SEQ ID NO: 52)
RGVTEDYLRLETLVQKVVSKGFYKKKQCRPSKGRKRGFCWAVD
```

Duplicate wells per dilution point in a 96-well NTA-coated plate (G-Biosciences, St. Louis, MO) charged with ferric chloride were adsorbed with 2 ug imm3N1V (V-nephrilin) or immX3N1 (sV-nephrilin) peptide per well for 30 min at room temperature, washed, then incubated with 100 ul/well of 8 or 2 μg/ml protease (Sigma Catalog #P4630, Pancreatic protease Type I) for 20 minutes at 37 degrees C. Plates were washed with PBS buffer and the remaining peptide bound was measured using an in-house calibrated anti-immodulin ELISA (rabbit polyclonal #2501). The percentages of surviving peptide after 8 or 2 μg/ml protease treatment were, respectively: V-nephrilin (imm3N1V): 57.6±2.3% and 79.0±0.7%; sV-nephrilin (immX3N1): 75.1±2.8% and 90.4±3.4% (p<0.001 at both concentrations). Thus, the immX tripeptide extension at the C-terminus using D-amino acids improved peptide stability to protease degradation.

Experiment 5B. This study explores the effect of immX extensions on sV-nephrilin (SEQ ID NO:31) vs V-nephrilin, as well as in a longer peptide also containing the immX extension (Traumatin-3N1A: SEQ ID NO:35) on in vivo efficacy in a rat scald-endotoxemia model. Animals were treated with peptides using a widely used protocol previously described (see, for example, U.S. Pat. No. 10,369,191). Adult Sprague Dawley rats of both sexes (250-300 gm, Charles River Laboratories, Wilmington, MA, USA) were injected with peptide plus equimolar ferric iron once daily by subcutaneous bolus injection, days 1-7; Treatment group sizes were (n=6): group S=sham-treated; group B=burn+vehicle; group V=burn+1 mg/kg V-nephrilin (V); group sV=burn+1 mg/kg sV-nephrilin (immX3N1sV); group T=burn+1 mg/kg Traumatin-3N1A. The first dose was administered after completion of the scald procedure. Injection volume was 400 uL. Control animals received the same volume of vehicle. On Day 8, animals received a single intraperitoneal injection of 2.5 mg/kg lipopolysaccharide (LPS; Sigma Cat #L-2880) and animals were then monitored by oximeter (MouseOx, Starr Life Sciences) for 4 hours, when respiratory distress (breath distension*breaths/min) was assessed relative to baseline. This was followed by sacrifice and tissue collection as in the published protocol, except that bronchoalveolar lavage (BAL) was collected and cells were recovered from BAL by centrifugation. These cells were stained with fluorescently-labeled antibodies for flow cytometry in order to ascertain granulocyte counts, as shown below. Results of the peptide comparison are presented in the table below. *p<0.05 vs "B" control. #p<0.05 vs "V" group.

| Day | | Group S | Group B | Group V | Group sV | Group T |
|---|---|---|---|---|---|---|
| 1 | Plasma albumin mg/ml (24 hr IR) | 3.6 ± 1.1* | 9.3 ± 1.2 | 7.9 ± 2.1 | 7.4 ± 1.6* | 7.6 ± 0.9* |
| 1 | Plasma IL-6 (pg/ml) | 24.6 ± 12.5* | 47.3 ± 18.5 | 31.4 ± 19 | 17.5 ± 9.3* | 22.5 ± 11* |

-continued

| Day | | Group S | Group B | Group V | Group sV | Group T |
|---|---|---|---|---|---|---|
| 5 | Change in body weight (Pct vs Day 1) | 7.0 ± 2.0* | −7.4 ± 1.2 | −9.8 ± 2.9 | −5.1 ± 3.6* | −5.3 ± 3.5* |
| 8 | Wet/dry lung weight (corrected for body weight) | 5.54 ± 0.64* | 8.27 ± 1.43 | 7.97 ± 0.76 | 7.07 ± 0.48* | 6.74 ± 0.61* |
| 8 | Respiratory distress (Gp. "S" = 100) | 100 ± 14*# | 322 ± 86 | 349 ± 95 | 203 ± 30*# | 197 ± 39*# |
| 8 | BAL fluid IL1-beta (pg/ml) | 13.8 ± 5*# | 139.6 ± 34 | 112.8 ± 9.4 | 67.1 ± 16*# | 45.7 ± 24*# |
| 8 | BAL His48+ granulocytes (FITC units) | 26.1 ± 4.9* | 34.7 ± 3.2 | 28.9 ± 3.1* | 26.8 ± 4.0* | ND |
| 8 | Plasma creatinine (mg/dL) | 0.65 ± 0.2* | 0.92 ± 0.1 | 0.91 ± 0.3 | 0.73 ± 0.2* | 0.64 ± 0.2* |
| 8 | Plasma OHDG (ng/ml) | 1.17 ± 0.8* | 2.18 ± 0.7 | 1.44 ± 1.0 | 1.31 ± 0.6* | 1.24 ± 0.4* |

Example 6. N-terminal modification of peptide with small molecules of molecular mass below 500 daltons that are not amino acids. N-terminal modification of peptides with biotin has been disclosed. This example shows the difficulty in predicting success for this type of modification for a previously untried small molecules. The data in this example disclose, amongst other facts: (i) efficient coupling to carboxylic acids that are not amino acids or biotin, is possible using normal peptide synthesis conditions; (ii) surprising results showing that yields of correctly coupled product (as ascertained by mass spectroscopy analysis) varies greatly, even within the same class of compound; and (iii) similar results were obtained for attachment to an immodulin peptide containing SEQ ID NO:2 or a generic D-tetrapeptide dLys-dAsp-dLys-dPro, with similar efficiencies of coupling to either peptide, thereby demonstrating the generality of the method. Peptides were synthesized according to a common Fmoc/tBu solid phase synthesis strategy well-known in the art. Synthesis may be manual of automated. After the peptide synthesis the resin was divided into batches of 20 umol. Each batch was treated with one of the organic compounds specified in the table shown immediately below. The coupling was carried out using 2 equivalents of the compound, 2.4 equivalents of activator HATU or HCTU, and 4 equivalents of NMM base. The reaction mixture was renewed after 2 hrs reaction time and allowed to react another 4 hrs or overnight. After washing the resin several times with DMF, and subsequently with DCM, the batches were dried. For the cleavage of the peptides from the resin the resins were treated with 1% DTT, 2% water and 3% TIPS in TFA for 3.5 hrs. The cleavage solution was separated from the resin and treated with diethylether/n-pentane (1:1). The resulting precipitate was centrifuged and the pellet washed three times in the same DEE/pentane mixture. The recovered peptide was air dried and stored at −20 degrees C. or further purified by HPLC using a 0-50% acetonitrile gradient, 0.1% trifuoroacetic acid (20 min). The results of the above conjugation experiments show that, both inter-class and intra-class, there is wide variation in conjugation efficiency from compound to compound. As the practicality and cost of synthesis can be dramatically affected when product yield is low, it is therefore not obvious that any untested carboxylic acid should be assumed to be a good candidate for this type of peptide modification. The use of most of the compounds tested here has never been reported for this kind of peptide modification. It appears that the chance of practical success (>80% correct yield, for instance) for each instantiation of this technology is less than 50% until tested.

| Class | Compound | CAS No. | MW | Yld T4* | Yld IM3* |
|---|---|---|---|---|---|
| fatty acid | oleic acid | 112-80-1 | 282.5 | 44.21% | |
| fatty acid | eicosapentaenoic acid | 10417-94-4 | 302.5 | 66.79% | |
| fatty acid | lignoceric acid | 557-59-5 | 368.6 | 89.20% | |
| fatty acid | decanoic acid | 1002-62-6 | 172.2 | 88.67% | 98.0% |
| fatty acid | docosahexanoic acid | 6217-54-5 | 368.6 | 57.77% | |
| fatty acid | lauric acid | 143-07-7 | 200.3 | 85.14% | 96.7% |
| fatty acid | 10-hydroxy-2-decenoic acid | 14113-05-4 | 186.3 | 44.38% | |
| phenolic acid | ferulic acid | 1135-24-6 | 194.2 | 26.58% | |
| phenolic acid | isoferulic acid | 537-73-5 | 194.2 | 55.80% | 70.2% |
| phenolic acid | Aspirin | 50-78-2 | 180.2 | 56.5% | |
| phenolic acid | valeroyl salicylate | 64206-54-8 | 222.2 | 11.76% | |
| pentacyclic | betulinic acid | 472-15-1 | 456.7 | <1% | |
| anthraquinone | Rhein | 478-43-3 | 284.2 | 50.95% | |
| anthraquinone | Diacerein | 13939-02-1 | 368.3 | 43.2% | |
| xanthone | 2,7-dichlorodihydro- | 4091-99-0 | 487.3 | 91.2% | |
| proprionic acid | (s)-ketoprofen | 22161-81-5 | 254.3 | 77.86% | |
| proprionic acid | Ibuprofen | 15687-27-1 | 206.3 | 93.42% | 98.0% |
| carboxylic acid | trans-cinnamic acid | 140-10-3 | 148.2 | 93.12% | 81.5% |
| carboxylic acid | (s)-(−)-perillic acid | 23635-14-5 | 166.2 | 27.96% | |
| carboxylic acid | fenofibric acid | 42017-89-0 | 318.8 | 85.67% | 99.9% |
| indoleacetic acid | Indomethacin | 53-86-1 | 357.8 | 87.5% | 85.2%# |
| pentanoic acid | valproic acid | 1069-66-5 | 144.2 | 91.43% | 84.9% |
| alkynoic acid | 2-hexyl-pentynoic acid | 96017-59-3 | 182.3 | | 85.1% |
| indolylcarboxylic | RG-108 | 48208-26-0 | 334.3 | | 74.3%@ |
| retinoid | all-trans retinoic acid | 302-79-4 | 300.4 | 13.1% | |
| rexinoid | Bexarotene | 153559-49-0 | 348.5 | 97.09% | 94.4% |

*% yield by MS for T4 (tetrapeptide) and imm3 peptide (>80% in bold type);
lost p-chlorophenone group;
@indole core oxidized by Arg (protecting gp);

Example 7. Anti-Cancer Actions of Immodulin Peptides

Immune modulation functions of immodulin peptides have great potential untility in the field of cancer. A375 cell line was obtained from American Type Culture Collection (ATCC). They were grown in a T-75 flask in DMEM Medium containing 10% fetal bovine serum and penicillin-streptomycin at 37° C. in a humidified, 5% $CO_2$ incubator. Cells (100 μl, 2,000 cells/well) were plated in a 96-well plate and incubated overnight at 37° C. in a humidified, 5% $CO_2$ incubator. Next day, 10 μl/well of compounds were added (quadruplicate wells). After 72 hour incubation with the compound, cell viability was measured in a luminometer after the addition of 100 IL/well CellTiterGlo reagent (Promega Inc, Madison, WI) as recommended by the manufacturer. Anti-cancer activity of immodulin peptides on A375 cells: A 96-well plate was seeded with 2,000 A375 cells per well in DMEM medium containing 10% FBS and PenStrep. After 24 hrs at 37 deg C., compounds and peptides were added (each treatment done in quadruplicate). After a further 72 hours incubation, 100 μL/well of CTG assay reagent purchased from Promega Inc. (Madison, WI) was added. Plate was read after 10 minutes, as recommended by the manufacturer. Peptides were added at 2 uM. The results of this experiment are shown below, expressed as percent survival of A375 cells. They show that anti-melanoma activity of various immodulin peptides are influenced by the core immodulin sequence, extension sequences, N-terminally conjugated carboxylic acids ±RIG-I agonist (4 uM). *$p<0.05$, **$p<0.01$ vs "no peptide" control; RIG-I ag=4 uM Cayman Chem. Co. Cat #22441; vlp=valproic; dec=decanoic; lau=lauric; rg108=RG108; h4p=h4-pentynoic; bpa=bromopyruvic; nd=not determined.

Example 8. Collagen Stimulating Activity of Immodulin Peptides

Immodulin peptides have potential untility in the field of cosmetics. HFF-1 human fibroblast cell line was obtained from the American Type Culture Collection (ATCC). Cells were grown in a T-75 flask in DMEM Medium containing 10% fetal bovine serum and penicillin-streptomycin at 37° C. in a humidified, 5% $CO_2$ incubator. Cells (100 μl, 2,000 cells/well) were plated in a 96-well plate and incubated overnight at 37° C. in a humidified, 5% $CO_2$ incubator. Next day, 10 μl/well of compounds were added (quadruplicate wells). After 72 hour incubation with the compound, supernatants were collected for Collagen-1 ELISA assay and cell viability was measured in a luminometer after the addition of 100 IL/well CellTiterGlo reagent (Promega Inc, Madison, WI) as recommended by the manufacturer. Collagen stimulating activity of immodulin peptides in HFF-1 dermal fibroblasts: Peptides were added to cells at 2 uM. COL1 immunoreactivity was measured in the supernatants of cultured cells by ELISA using a rabbit monoclonal anti-COL1 primary antibody (Abcam, Cambridge, MA). The results of this experiment are shown in Table above. Control (buffer) value of immunoreactivity was set to 100. The data show that collagen stimulating activity of various immodulin peptides are influenced by specific extension sequences and by N-terminally conjugated carboxylic acids. *$p<0.05$, **$p<0.01$ vs "no peptide" control; bex=bexarotene; isf=isoferulic; vlp=valproic; dec=decanoic; cin=cinnamic; rhn=rhein;

| Peptide | Sequence | Buffer | +RIG-I ag | SEQ ID NO: |
|---|---|---|---|---|
| | No peptide | 100 | 100.7 | |
| imm1 | KNGFYHSRQCETSMDGEAGLCW | 102.1 | Nd | 42 |
| imm2 | KHGLYNLKQCKMSLNGQRGECW | 99.0 | Nd | 43 |
| imm3 | KKGFYKKKQCRPSKGRKRGFCW | 100.3 | 62.2** | 44 |
| imm4 | RNGNFHPKQCHPALDGQRGKCW | 98.8 | Nd | 45 |
| imm5 | RKGFYKRKQCKPSRGRKRGICW | 103.4 | Nd | 46 |
| imm6 | HRGFYRKRQCRSSQGQRRGPCW | 102.2 | Nd | 47 |
| imm3avd | KKGFYKKKQCRPSKGRKRGFCWAVD | 96.0 | 12.5** | 13 |
| imm3fvs | KKGFYKKKQCRPSKGRKRGFCWFVS | 96.1 | 22.6** | 49 |
| imm3vlp | (vlp)-KKGFYKKKQCRPSKGRKRGFCW | 93.9** | 32.6** | 44 |
| imm3dec | (dec)-KKGFYKKKQCRPSKGRKRGFCW | 89.0** | 53.8** | 44 |
| imm3lau | (lau)-KKGFYKKKQCRPSKGRKRGFCW | 96.6* | 17.4** | 44 |
| imm3rg8 | (rg108)-KKGFYKKKQCRPSKGRKRGFCW | 89.9** | 105.8 | 44 |
| imm3h4p | (h4p)-KKGFYKKKQCRPSKGRKRGFCW | 91.7** | Nd | 44 |
| imm3K1 | SLNPEWNETKGFYKKKQCRPSKGRKRGFCW | 92.5** | 17.0** | 55 |
| imm3K1bpa | (bpa)SLNPEWNETKGFYKKKQCRPSKGRKRGFCW | 98.4 | Nd | 55 |
| imm3K1.1 | SLNPEWNETKKGFYKKKQCRPSKGRKRGFCW | 95.3* | Nd | 54 |

| Peptide | Sequence | COL1 | SEQ ID NO |
|---|---|---|---|
| | No peptide | 100 | |
| imm1 | KNGFYHSRQCETSMDGEAGLCW | 98 | 42 |
| imm2 | KHGLYNLKQCKMSLNGQRGECW | 109 | 43 |
| imm3 | KKGFYKKKQCRPSKGRKRGFCW | 101 | 44 |
| imm4 | RNGNFHPKQCHPALDGQRGKCW | 105 | 45 |
| imm5 | RKGFYKRKQCKPSRGRKRGICW | 93 | 46 |
| imm6 | HRGFYRKRQCRSSQGQRRGPCW | 112 | 47 |
| imm3bex | (bex)-KKGFYKKKQCRPSKGRKRGFCW | 102 | 44 |
| imm3isf | (isf)-KKGFYKKKQCRPSKGRKRGFCW | 131* | 44 |
| imm3vlp | (vlp)-KKGFYKKKQCRPSKGRKRGFCW | 157** | 44 |
| imm3dec | (dec)-KKGFYKKKQCRPSKGRKRGFCW | 114 | 44 |
| imm3cin | (cin)-KKGFYKKKQCRPSKGRKRGFCW | 106 | 44 |
| imm3rhn | (rhn)-KKGFYKKKQCRPSKGRKRGFCW | 68** | 44 |
| imm3K9 | AFNSYELGSKGFYKKKQCRPSKGRKRGFCW | 155** | 56 |
| imm3K9.1 | AFNSYELGSKKGFYKKKQCRPSKGRKRGFCW | 156** | 57 |
| imm3K9c | AFNSYELGSKGFYKKKQCRPSKGRKRGFCWAVDKY | 158** | 58 |
| imm3K8 | FNSYELGSLKKGFYKKKQCRPSKGRKRGFCW | 98 | 59 |

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Incorporation by Reference of Sequence Listing file: Sequence Listing is entered into the application as part of the disclosure. Date of Creation: Jul. 8, 2025; Size of txt file in bytes: 22,321 bytes.

Name of file: 18264181_SEQfile_070825.txt

What is claimed is:

1. A method for stimulating the relative abundance or biological activity of a differentiation marker in a mammalian hematopoietic cell lineage in vivo or ex vivo, comprising:
   (i) contacting one or more live mammalian cells in vivo or ex vivo with a synthetic immodulin peptide, 20-60 amino acids in length, comprising an amino acid sequence corresponding to any one of SEQ ID NOs: 1-7 wherein the synthetic immodulin peptide is covalently attached to a non-amino acid small molecule of molecular mass less than one thousand daltons; and
   (ii) following the contacting step, measuring the abundance or biological activity of a marker distinctive for the differentiated cell lineage, wherein said marker is CD169;
   (iii) optimizing the dose of the synthetic immodulin peptide based on said measurement; thereby demonstrating that the optimized dose of the synthetic immodulin peptide stimulated the relative abundance or biological activity of the differentiated cell lineage.

2. The method according to claim 1, wherein the synthetic immodulin peptide comprises an amino acid sequence corresponding to any one of SEQ ID NOs: 4-7.

3. The method according to claim 1, comprising administration to a mammal of a therapeutically effective dose of the synthetic immodulin peptide wherein said therapeutically effective dose of the synthetic peptide is from about 0.01 mg/kg/day to about 50 mg/kg/day.

4. A synthetic immodulin peptide, 20-60 amino acids in length, comprising an amino acid sequence corresponding to any one of SEQ ID NOs: 4-7.

5. The synthetic immodulin peptide according to claim 4, further comprising an amino acid sequence selected from the group consisting of SEQ ID NOs: 8-12.

6. The synthetic immodulin peptide according to claim 4 co-formulated with a metal selected from the group consisting of: ferrous iron, ferric iron, ferrocene, zinc, copper, vanadium, ruthenium, cobalt, titanium, manganese, and calcium.

7. The synthetic immodulin peptide according to claim 4 co-formulated with a molecule selected from the group consisting of: transferrin, gallic acid, methyl gallate, gallocyanine, heparin, chondroitin sulfate, keratan sulfate, dermatan sulfate, and hyaluronic acid.

* * * * *

SEQUENCE LISTING

```
<160> NUMBER OF SEQ IDS: 62

<210> SEQ ID NO 1
<211> LENGTH: 21
<212> TYPE: PRT
<213> ORGANISM: Artificial Sequence
<220> FEATURE:
<223> OTHER INFORMATION: Synthetic

<400> SEQUENCE: 1

Lys Gly Phe Tyr Lys Lys Lys Gln Cys Arg Pro Ser Lys Gly Arg Lys
1               5                   10                  15

Arg Gly Phe Cys Trp
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic

<400> SEQUENCE: 2
```

-continued

Lys Gly Phe Tyr Lys Arg Lys Gln Cys Lys Pro Ser Arg Gly Arg Lys
1               5                   10                  15

Arg Gly Ile Cys Trp
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic

<400> SEQUENCE: 3

Arg Gly Phe Tyr Arg Lys Arg Gln Cys Arg Ser Ser Gln Gly Gln Arg
1               5                   10                  15

Arg Gly Pro Cys Trp
            20

<210> SEQ ID NO 4
<211> LENGTH: 24
<212> TYPE: PRT
<213> ORGANISM: Artificial Sequence
<220> FEATURE:
<223> OTHER INFORMATION: Synthetic

<400> SEQUENCE: 4

Lys Gly Phe Tyr Lys Lys Lys Gln Cys Arg Pro Ser Lys Gly Arg Lys
1               5                   10                  15

Arg Gly Phe Cys Trp Ser Val Asp
            20

<210> SEQ ID NO 5
<211> LENGTH: 24
<212> TYPE: PRT
<213> ORGANISM: Artificial Sequence
<220> FEATURE:
<223> OTHER INFORMATION: Synthetic

<400> SEQUENCE: 5

Lys Gly Phe Tyr Lys Arg Lys Gln Cys Lys Pro Ser Arg Gly Arg Lys
1               5                   10                  15

Arg Gly Ile Cys Trp Ser Val Asp
            20

<210> SEQ ID NO 6
<211> LENGTH: 24
<212> TYPE: PRT
<213> ORGANISM: Artificial Sequence
<220> FEATURE:
<223> OTHER INFORMATION: Synthetic

<400> SEQUENCE: 6

Arg Gly Phe Tyr Arg Lys Arg Gln Cys Arg Ser Ser Gln Gly Gln Arg
1               5                   10                  15

Arg Gly Pro Cys Trp Ser Val Asp
            20

<210> SEQ ID NO 7
<211> LENGTH: 24
<212> TYPE: PRT
<213> ORGANISM: Artificial sequence
<220> FEATURE:
<223> OTHER INFORMATION: Synthetic

<400> SEQUENCE: 7

Lys Gly Phe Tyr Lys Arg Lys Gln Cys Lys Pro Ser Arg Gly Arg Lys
1               5                   10                  15

Arg Gly Ile Cys Trp Ala Val Asp
            20

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Ser Leu Asn Pro Glu Trp Asn Glu Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Ala Phe Asn Ser Tyr Glu Leu Gly Ser
1               5

<210> SEQ ID NO 10
<211> LENGTH: 18
<212> TYPE: PRT
<213> ORGANISM: Artificial Sequence
<220> FEATURE:
<223> OTHER INFORMATION: Synthetic

<400> SEQUENCE: 10

Gly Val Thr Glu Asp Tyr Leu Arg Leu Glu Thr Leu Val Gln Lys Val
1               5                   10                  15

Val Ser

<210> SEQ ID NO 11
<211> LENGTH: 18
<212> TYPE: PRT
<213> ORGANISM: Artificial Sequence
<220> FEATURE:
<223> OTHER INFORMATION: Synthetic

<400> SEQUENCE: 11

Gly Pro Ser Glu Ser Tyr Leu Gln Leu Glu Glu Leu Val Lys Gln Val
1               5                   10                  15

Val Ser

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

Glu Arg Asn Ala Tyr Arg Ala Ser Ile Lys Gln
1               5                   10

<210> SEQ ID NO 13
<211> LENGTH: 25

```
<212> TYPE: PRT
<213> ORGANISM: Artificial Sequence
<220> FEATURE:
<223> OTHER INFORMATION: Synthetic

<400> SEQUENCE: 13

Lys Lys Gly Phe Tyr Lys Lys Lys Gln Cys Arg Pro Ser Lys Gly Arg
1               5                   10                  15

Lys Arg Gly Phe Cys Trp Ala Val Asp
            20                  25

<210> SEQ ID NO 14
<211> LENGTH: 25
<212> TYPE: PRT
<213> ORGANISM: Artificial Sequence
<220> FEATURE:
<223> OTHER INFORMATION: Synthetic

<400> SEQUENCE: 14

Lys Lys Gly Phe Tyr Lys Lys Lys Gln Cys Arg Pro Ser Lys Gly Arg
1               5                   10                  15

Lys Arg Gly Phe Cys Trp Ser Val Asp
            20                  25

<210> SEQ ID NO 15
<211> LENGTH: 25
<212> TYPE: PRT
<213> ORGANISM: Artificial Sequence
<220> FEATURE:
<223> OTHER INFORMATION: Synthetic

<400> SEQUENCE: 15

Arg Lys Gly Phe Tyr Lys Arg Lys Gln Cys Lys Pro Ser Arg Gly Arg
1               5                   10                  15

Lys Arg Gly Ile Cys Trp Ala Val Asp
            20                  25

<210> SEQ ID NO 16
<211> LENGTH: 25
<212> TYPE: PRT
<213> ORGANISM: Artificial Sequence
<220> FEATURE:
<223> OTHER INFORMATION: Synthetic

<400> SEQUENCE: 16

Arg Lys Gly Phe Tyr Lys Arg Lys Gln Cys Lys Pro Ser Arg Gly Arg
1               5                   10                  15

Lys Arg Gly Ile Cys Trp Ser Val Asp
            20                  25

<210> SEQ ID NO 17
<211> LENGTH: 25
<212> TYPE: PRT
<213> ORGANISM: Artificial Sequence
<220> FEATURE:
<223> OTHER INFORMATION: Synthetic

<400> SEQUENCE: 17

His Arg Gly Phe Tyr Arg Lys Arg Gln Cys Arg Ser Ser Gln Gly Gln
1               5                   10                  15

Arg Arg Gly Pro Cys Trp Ala Val Asp
            20                  25

<210> SEQ ID NO 18
```

```
<211> LENGTH: 25
<212> TYPE: PRT
<213> ORGANISM: Artificial Sequence
<220> FEATURE:
<223> OTHER INFORMATION: Synthetic

<400> SEQUENCE: 18

His Arg Gly Phe Tyr Arg Lys Arg Gln Cys Arg Ser Ser Gln Gly Gln
1               5                   10                  15

Arg Arg Gly Pro Cys Trp Ser Val Asp
            20                  25

<210> SEQ ID NO 19
<211> LENGTH: 33
<212> TYPE: PRT
<213> ORGANISM: Artificial Sequence
<220> FEATURE:
<223> OTHER INFORMATION: Synthetic

<400> SEQUENCE: 19

Ser Leu Asn Pro Glu Trp Asn Glu Thr Lys Gly Phe Tyr Lys Lys Lys
1               5                   10                  15

Gln Cys Arg Pro Ser Lys Gly Arg Lys Arg Gly Phe Cys Trp Ala Val
            20                  25                  30

Asp

<210> SEQ ID NO 20
<211> LENGTH: 33
<212> TYPE: PRT
<213> ORGANISM: Artificial Sequence
<220> FEATURE:
<223> OTHER INFORMATION: Synthetic

<400> SEQUENCE: 20

Ser Leu Asn Pro Glu Trp Asn Glu Thr Lys Gly Phe Tyr Lys Lys Lys
1               5                   10                  15

Gln Cys Arg Pro Ser Lys Gly Arg Lys Arg Gly Phe Cys Trp Ser Val
            20                  25                  30

Asp

<210> SEQ ID NO 21
<211> LENGTH: 33
<212> TYPE: PRT
<213> ORGANISM: Artificial Sequence
<220> FEATURE:
<223> OTHER INFORMATION: Synthetic

<400> SEQUENCE: 21

Ser Leu Asn Pro Glu Trp Asn Glu Thr Lys Gly Phe Tyr Lys Arg Lys
1               5                   10                  15

Gln Cys Lys Pro Ser Arg Gly Arg Lys Arg Gly Ile Cys Trp Ala Val
            20                  25                  30

Asp

<210> SEQ ID NO 22
<211> LENGTH: 33
<212> TYPE: PRT
<213> ORGANISM: Artificial Sequence
<220> FEATURE:
<223> OTHER INFORMATION: Synthetic

<400> SEQUENCE: 22

Ser Leu Asn Pro Glu Trp Asn Glu Thr Lys Gly Phe Tyr Lys Arg Lys
```

```
                1               5                  10                  15
Gln Cys Lys Pro Ser Arg Gly Arg Lys Arg Gly Ile Cys Trp Ser Val
                20                  25                  30
Asp

<210> SEQ ID NO 23
<211> LENGTH: 33
<212> TYPE: PRT
<213> ORGANISM: Artificial Sequence
<220> FEATURE:
<223> OTHER INFORMATION: Synthetic

<400> SEQUENCE: 23

Ser Leu Asn Pro Glu Trp Asn Glu Thr Arg Gly Phe Tyr Arg Lys Arg
1               5                  10                  15
Gln Cys Arg Ser Ser Gln Gly Gln Arg Arg Gly Pro Cys Trp Ala Val
                20                  25                  30
Asp

<210> SEQ ID NO 24
<211> LENGTH: 33
<212> TYPE: PRT
<213> ORGANISM: Artificial Sequence
<220> FEATURE:
<223> OTHER INFORMATION: Synthetic

<400> SEQUENCE: 24

Ser Leu Asn Pro Glu Trp Asn Glu Thr Arg Gly Phe Tyr Arg Lys Arg
1               5                  10                  15
Gln Cys Arg Ser Ser Gln Gly Gln Arg Arg Gly Pro Cys Trp Ser Val
                20                  25                  30
Asp

<210> SEQ ID NO 25
<211> LENGTH: 33
<212> TYPE: PRT
<213> ORGANISM: Artificial Sequence
<220> FEATURE:
<223> OTHER INFORMATION: Synthetic

<400> SEQUENCE: 25

Ala Phe Asn Ser Tyr Glu Leu Gly Ser Lys Gly Phe Tyr Lys Lys Lys
1               5                  10                  15
Gln Cys Arg Pro Ser Lys Gly Arg Lys Arg Gly Phe Cys Trp Ala Val
                20                  25                  30
Asp

<210> SEQ ID NO 26
<211> LENGTH: 33
<212> TYPE: PRT
<213> ORGANISM: Artificial Sequence
<220> FEATURE:
<223> OTHER INFORMATION: Synthetic

<400> SEQUENCE: 26

Ala Phe Asn Ser Tyr Glu Leu Gly Ser Lys Gly Phe Tyr Lys Lys Lys
1               5                  10                  15
Gln Cys Arg Pro Ser Lys Gly Arg Lys Arg Gly Phe Cys Trp Ser Val
                20                  25                  30
Asp
```

<210> SEQ ID NO 27
<211> LENGTH: 33
<212> TYPE: PRT
<213> ORGANISM: Artificial Sequence
<220> FEATURE:
<223> OTHER INFORMATION: Synthetic

<400> SEQUENCE: 27

```
Ala Phe Asn Ser Tyr Glu Leu Gly Ser Lys Gly Phe Tyr Lys Arg Lys
1               5                   10                  15

Gln Cys Lys Pro Ser Arg Gly Arg Lys Arg Gly Ile Cys Trp Ala Val
            20                  25                  30

Asp
```

<210> SEQ ID NO 28
<211> LENGTH: 33
<212> TYPE: PRT
<213> ORGANISM: Artificial Sequence
<220> FEATURE:
<223> OTHER INFORMATION: Synthetic

<400> SEQUENCE: 28

```
Ala Phe Asn Ser Tyr Glu Leu Gly Ser Lys Gly Phe Tyr Lys Arg Lys
1               5                   10                  15

Gln Cys Lys Pro Ser Arg Gly Arg Lys Arg Gly Ile Cys Trp Ser Val
            20                  25                  30

Asp
```

<210> SEQ ID NO 29
<211> LENGTH: 33
<212> TYPE: PRT
<213> ORGANISM: Artificial Sequence
<220> FEATURE:
<223> OTHER INFORMATION: Synthetic

<400> SEQUENCE: 29

```
Ala Phe Asn Ser Tyr Glu Leu Gly Ser Arg Gly Phe Tyr Arg Lys Arg
1               5                   10                  15

Gln Cys Arg Ser Ser Gln Gly Gln Arg Arg Gly Pro Cys Trp Ala Val
            20                  25                  30

Asp
```

<210> SEQ ID NO 30
<211> LENGTH: 33
<212> TYPE: PRT
<213> ORGANISM: Artificial Sequence
<220> FEATURE:
<223> OTHER INFORMATION: Synthetic

<400> SEQUENCE: 30

```
Ala Phe Asn Ser Tyr Glu Leu Gly Ser Arg Gly Phe Tyr Arg Lys Arg
1               5                   10                  15

Gln Cys Arg Ser Ser Gln Gly Gln Arg Arg Gly Pro Cys Trp Ser Val
            20                  25                  30

Asp
```

<210> SEQ ID NO 31
<211> LENGTH: 43
<212> TYPE: PRT
<213> ORGANISM: Artificial Sequence
<220> FEATURE:
<223> OTHER INFORMATION: Synthetic

<400> SEQUENCE: 31

Arg Gly Val Thr Glu Asp Tyr Leu Arg Leu Glu Thr Leu Val Gln Lys
1               5                   10                  15

Val Val Ser Lys Gly Phe Tyr Lys Lys Gln Cys Arg Pro Ser Lys
            20                  25                  30

Gly Arg Lys Arg Gly Phe Cys Trp Ala Val Asp
        35                  40

<210> SEQ ID NO 32
<211> LENGTH: 43
<212> TYPE: PRT
<213> ORGANISM: Artificial Sequence
<220> FEATURE:
<223> OTHER INFORMATION: Synthetic

<400> SEQUENCE: 32

Arg Gly Val Thr Glu Asp Tyr Leu Arg Leu Glu Thr Leu Val Gln Lys
1               5                   10                  15

Val Val Ser Lys Gly Phe Tyr Lys Lys Gln Cys Arg Pro Ser Lys
            20                  25                  30

Gly Arg Lys Arg Gly Phe Cys Trp Ser Val Asp
        35                  40

<210> SEQ ID NO 33
<211> LENGTH: 43
<212> TYPE: PRT
<213> ORGANISM: Artificial Sequence
<220> FEATURE:
<223> OTHER INFORMATION: Synthetic

<400> SEQUENCE: 33

Thr Gly Pro Ser Glu Ser Tyr Leu Gln Leu Glu Leu Val Lys Gln
1               5                   10                  15

Val Val Ser Lys Gly Phe Tyr Lys Lys Gln Cys Arg Pro Ser Lys
            20                  25                  30

Gly Arg Lys Arg Gly Phe Cys Trp Ser Val Asp
        35                  40

<210> SEQ ID NO 34
<211> LENGTH: 43
<212> TYPE: PRT
<213> ORGANISM: Artificial Sequence
<220> FEATURE:
<223> OTHER INFORMATION: Synthetic

<400> SEQUENCE: 34

Arg Gly Val Thr Glu Asp Tyr Leu Arg Leu Glu Thr Leu Val Gln Lys
1               5                   10                  15

Val Val Ser Lys Gly Phe Tyr Lys Arg Lys Gln Cys Lys Pro Ser Arg
            20                  25                  30

Gly Arg Lys Arg Gly Ile Cys Trp Ser Val Asp
        35                  40

<210> SEQ ID NO 35
<211> LENGTH: 46
<212> TYPE: PRT
<213> ORGANISM: Artificial Sequence
<220> FEATURE:
<223> OTHER INFORMATION: Synthetic

<400> SEQUENCE: 35

Arg Gly Val Thr Glu Asp Tyr Leu Arg Leu Glu Thr Leu Val Gln Lys
1               5                   10                  15

Val Val Ser Pro Tyr Leu Lys Gly Phe Tyr Lys Lys Lys Gln Cys Arg
            20                  25                  30

Pro Ser Lys Gly Arg Lys Arg Gly Phe Cys Trp Ala Val Asp
        35                  40                  45

<210> SEQ ID NO 36
<211> LENGTH: 46
<212> TYPE: PRT
<213> ORGANISM: Artificial Sequence
<220> FEATURE:
<223> OTHER INFORMATION: Synthetic

<400> SEQUENCE: 36

Arg Gly Val Thr Glu Asp Tyr Leu Arg Leu Glu Thr Leu Val Gln Lys
1               5                   10                  15

Val Val Ser Pro Tyr Leu Lys Gly Phe Tyr Lys Lys Lys Gln Cys Arg
            20                  25                  30

Pro Ser Lys Gly Arg Lys Arg Gly Phe Cys Trp Ser Val Asp
        35                  40                  45

<210> SEQ ID NO 37
<211> LENGTH: 46
<212> TYPE: PRT
<213> ORGANISM: Artificial Sequence
<220> FEATURE:
<223> OTHER INFORMATION: Synthetic

<400> SEQUENCE: 37

Arg Gly Val Thr Glu Asp Tyr Leu Arg Leu Glu Thr Leu Val Gln Lys
1               5                   10                  15

Val Val Ser Pro Tyr Leu Lys Gly Phe Tyr Lys Arg Lys Gln Cys Lys
            20                  25                  30

Pro Ser Arg Gly Arg Lys Arg Gly Ile Cys Trp Ser Val Asp
        35                  40                  45

<210> SEQ ID NO 38
<211> LENGTH: 46
<212> TYPE: PRT
<213> ORGANISM: Artificial Sequence
<220> FEATURE:
<223> OTHER INFORMATION: Synthetic

<400> SEQUENCE: 38

Thr Gly Pro Ser Glu Ser Tyr Leu Gln Leu Glu Glu Leu Val Lys Gln
1               5                   10                  15

Val Val Ser Pro Tyr Leu Lys Gly Phe Tyr Lys Lys Lys Gln Cys Arg
            20                  25                  30

Pro Ser Lys Gly Arg Lys Arg Gly Phe Cys Trp Ser Val Asp
        35                  40                  45

<210> SEQ ID NO 39
<211> LENGTH: 20
<212> TYPE: PRT
<213> ORGANISM: Artificial Sequence
<220> FEATURE:
<223> OTHER INFORMATION: Synthetic

<400> SEQUENCE: 39

Gly Phe Tyr Lys Lys Lys Gln Cys Arg Pro Ser Lys Gly Arg Lys Arg
1               5                   10                  15

Gly Phe Cys Trp
            20

<210> SEQ ID NO 40
<211> LENGTH: 20
<212> TYPE: PRT
<213> ORGANISM: Artificial Sequence
<220> FEATURE:
<223> OTHER INFORMATION: Synthetic

<400> SEQUENCE: 40

Gly Phe Tyr Lys Arg Lys Gln Cys Lys Pro Ser Arg Gly Arg Lys Arg
1               5                   10                  15

Gly Ile Cys Trp
            20

<210> SEQ ID NO 41
<211> LENGTH: 20
<212> TYPE: PRT
<213> ORGANISM: Artificial Sequence
<220> FEATURE:
<223> OTHER INFORMATION: Synthetic

<400> SEQUENCE: 41

Gly Phe Tyr Arg Lys Arg Gln Cys Arg Ser Ser Gln Gly Gln Arg Arg
1               5                   10                  15

Gly Pro Cys Trp
            20

<210> SEQ ID NO 42
<211> LENGTH: 22
<212> TYPE: PRT
<213> ORGANISM: Artificial Sequence
<220> FEATURE:
<223> OTHER INFORMATION: Synthetic

<400> SEQUENCE: 42

Lys Asn Gly Phe Tyr His Ser Arg Gln Cys Glu Thr Ser Met Asp Gly
1               5                   10                  15

Glu Ala Gly Leu Cys Trp
            20

<210> SEQ ID NO 43
<211> LENGTH: 22
<212> TYPE: PRT
<213> ORGANISM: Artificial Sequence
<220> FEATURE:
<223> OTHER INFORMATION: Synthetic

<400> SEQUENCE: 43

Lys His Gly Leu Tyr Asn Leu Lys Gln Cys Lys Met Ser Leu Asn Gly
1               5                   10                  15

Gln Arg Gly Glu Cys Trp
            20

<210> SEQ ID NO 44
<211> LENGTH: 22
<212> TYPE: PRT
<213> ORGANISM: Artificial Sequence
<220> FEATURE:
<223> OTHER INFORMATION: Synthetic

<400> SEQUENCE: 44

Lys Lys Gly Phe Tyr Lys Lys Lys Gln Cys Arg Pro Ser Lys Gly Arg
1               5                   10                  15

```
Lys Arg Gly Phe Cys Trp
            20

<210> SEQ ID NO 45
<211> LENGTH: 22
<212> TYPE: PRT
<213> ORGANISM: Artificial Sequence
<220> FEATURE:
<223> OTHER INFORMATION: Synthetic

<400> SEQUENCE: 45

Arg Asn Gly Asn Phe His Pro Lys Gln Cys His Pro Ala Leu Asp Gly
1               5                   10                  15

Gln Arg Gly Lys Cys Trp
            20

<210> SEQ ID NO 46
<211> LENGTH: 22
<212> TYPE: PRT
<213> ORGANISM: Artificial Sequence
<220> FEATURE:
<223> OTHER INFORMATION: Synthetic

<400> SEQUENCE: 46

Arg Lys Gly Phe Tyr Lys Arg Lys Gln Cys Lys Pro Ser Arg Gly Arg
1               5                   10                  15

Lys Arg Gly Ile Cys Trp
            20

<210> SEQ ID NO 47
<211> LENGTH: 22
<212> TYPE: PRT
<213> ORGANISM: Artificial Sequence
<220> FEATURE:
<223> OTHER INFORMATION: Synthetic

<400> SEQUENCE: 47

His Arg Gly Phe Tyr Arg Lys Arg Gln Cys Arg Ser Ser Gln Gly Gln
1               5                   10                  15

Arg Arg Gly Pro Cys Trp
            20

<210> SEQ ID NO 48
<211> LENGTH: 25
<212> TYPE: PRT
<213> ORGANISM: Artificial Sequence
<220> FEATURE:
<223> OTHER INFORMATION: Synthetic

<400> SEQUENCE: 48

Arg Asn Gly Asn Phe His Pro Lys Gln Cys His Pro Ala Leu Asp Gly
1               5                   10                  15

Gln Arg Gly Lys Cys Trp Ala Val Asp
            20                  25

<210> SEQ ID NO 49
<211> LENGTH: 25
<212> TYPE: PRT
<213> ORGANISM: Artificial Sequence
<220> FEATURE:
<223> OTHER INFORMATION: Synthetic

<400> SEQUENCE: 49

Lys Lys Gly Phe Tyr Lys Lys Lys Gln Cys Arg Pro Ser Lys Gly Arg
```

```
1               5                   10                  15
Lys Arg Gly Phe Cys Trp Phe Val Ser
            20                  25

<210> SEQ ID NO 50
<211> LENGTH: 25
<212> TYPE: PRT
<213> ORGANISM: Artificial Sequence
<220> FEATURE:
<223> OTHER INFORMATION: Synthetic

<400> SEQUENCE: 50

Lys Lys Gly Phe Tyr Lys Lys Lys Gln Cys Arg Pro Ser Lys Gly Arg
1               5                   10                  15
Lys Arg Gly Phe Cys Trp Arg Val Asp
            20                  25

<210> SEQ ID NO 51
<211> LENGTH: 40
<212> TYPE: PRT
<213> ORGANISM: Artificial Sequence
<220> FEATURE:
<223> OTHER INFORMATION: Synthetic

<400> SEQUENCE: 51

Arg Gly Val Thr Glu Asp Tyr Leu Arg Leu Glu Thr Leu Val Gln Lys
1               5                   10                  15
Val Val Ser Lys Gly Phe Tyr Lys Lys Gln Cys Arg Pro Ser Lys
            20                  25                  30
Gly Arg Lys Arg Gly Phe Cys Trp
            35                  40

<210> SEQ ID NO 52
<211> LENGTH: 43
<212> TYPE: PRT
<213> ORGANISM: Artificial Sequence
<220> FEATURE:
<223> OTHER INFORMATION: Synthetic

<400> SEQUENCE: 52

Arg Gly Val Thr Glu Asp Tyr Leu Arg Leu Glu Thr Leu Val Gln Lys
1               5                   10                  15
Val Val Ser Lys Gly Phe Tyr Lys Lys Gln Cys Arg Pro Ser Lys
            20                  25                  30
Gly Arg Lys Arg Gly Phe Cys Trp Ala Val Asp
            35                  40

<210> SEQ ID NO 53
<211> LENGTH: 33
<212> TYPE: PRT
<213> ORGANISM: Artificial Sequence
<220> FEATURE:
<223> OTHER INFORMATION: Synthetic

<400> SEQUENCE: 53

Ser Leu Asn Pro Glu Trp Asn Glu Thr Lys Gly Phe Tyr Lys Lys
1               5                   10                  15
Gln Cys Arg Pro Ser Lys Gly Arg Lys Arg Gly Phe Cys Trp Ala Val
            20                  25                  30
Asp

<210> SEQ ID NO 54
```

<211> LENGTH: 31
<212> TYPE: PRT
<213> ORGANISM: Artificial Sequence
<220> FEATURE:
<223> OTHER INFORMATION: Synthetic

<400> SEQUENCE: 54

Ser Leu Asn Pro Glu Trp Asn Glu Thr Lys Lys Gly Phe Tyr Lys Lys
1               5                   10                  15

Lys Gln Cys Arg Pro Ser Lys Gly Arg Lys Arg Gly Phe Cys Trp
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: Synthetic

<400> SEQUENCE: 55

Ser Leu Asn Pro Glu Trp Asn Glu Thr Lys Gly Phe Tyr Lys Lys
1               5                   10                  15

Gln Cys Arg Pro Ser Lys Gly Arg Lys Arg Gly Phe Cys Trp
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: Synthetic

<400> SEQUENCE: 56

Ala Phe Asn Ser Tyr Glu Leu Gly Ser Lys Gly Phe Tyr Lys Lys
1               5                   10                  15

Gln Cys Arg Pro Ser Lys Gly Arg Lys Arg Gly Phe Cys Trp
            20                  25                  30

<210> SEQ ID NO 57
<211> LENGTH: 31
<212> TYPE: PRT
<213> ORGANISM: Artificial Sequence
<220> FEATURE:
<223> OTHER INFORMATION: Synthetic

<400> SEQUENCE: 57

Ala Phe Asn Ser Tyr Glu Leu Gly Ser Lys Lys Gly Phe Tyr Lys Lys
1               5                   10                  15

Lys Gln Cys Arg Pro Ser Lys Gly Arg Lys Arg Gly Phe Cys Trp
            20                  25                  30

<210> SEQ ID NO 58
<211> LENGTH: 35
<212> TYPE: PRT
<213> ORGANISM: Artificial Sequence
<220> FEATURE:
<223> OTHER INFORMATION: Synthetic

<400> SEQUENCE: 58

Ala Phe Asn Ser Tyr Glu Leu Gly Ser Lys Gly Phe Tyr Lys Lys
1               5                   10                  15

Gln Cys Arg Pro Ser Lys Gly Arg Lys Arg Gly Phe Cys Trp Ala Val
            20                  25                  30

Asp Lys Tyr

```
<210> SEQ ID NO 59
<211> LENGTH: 31
<212> TYPE: PRT
<213> ORGANISM: Artificial Sequence
<220> FEATURE:
<223> OTHER INFORMATION: Synthetic

<400> SEQUENCE: 59

Phe Asn Ser Tyr Glu Leu Gly Ser Leu Lys Lys Gly Phe Tyr Lys Lys
1               5                   10                  15

Lys Gln Cys Arg Pro Ser Lys Gly Arg Lys Arg Gly Phe Cys Trp
            20                  25                  30

<210> SEQ ID NO 60
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(23)
<223> OTHER INFORMATION: Xaa is any amino acid except cysteine

<400> SEQUENCE: 60

Gly Phe Tyr Lys Lys Lys Gln Cys Arg Pro Ser Lys Gly Arg Lys Arg
1               5                   10                  15

Gly Phe Cys Trp Xaa Val Asp
            20

<210> SEQ ID NO 61
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(23)
<223> OTHER INFORMATION: Xaa is any amino acid except cysteine

<400> SEQUENCE: 61

Gly Phe Tyr Lys Arg Lys Gln Cys Lys Pro Ser Arg Gly Arg Lys Arg
1               5                   10                  15

Gly Ile Cys Trp Xaa Val Asp
            20

<210> SEQ ID NO 62
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(23)
<223> OTHER INFORMATION: Xaa is any amino acid except cysteine

<400> SEQUENCE: 62

Gly Phe Tyr Arg Lys Arg Gln Cys Arg Ser Ser Gln Gly Gln Arg Arg
1               5                   10                  15

Gly Pro Cys Trp Xaa Val Asp
            20
```